United States Patent
Sunshine et al.

(10) Patent No.: US 6,837,095 B2
(45) Date of Patent: Jan. 4, 2005

(54) APPARATUS, SYSTEMS AND METHODS FOR DETECTING AND TRANSMITTING SENSORY DATA OVER A COMPUTER NETWORK

(75) Inventors: Steven A. Sunshine, Pasadena, CA (US); Gregory Steinthal, Los Angeles, CA (US); Christopher K. Boehr, San Gabriel, CA (US); Robert K. Nakayama, Los Angeles, CA (US)

(73) Assignee: Smiths Detection - Pasadena, Inc., Pasadena, CA (US)

( * ) Notice: Subject to any disclaimer, the term of this patent is extended or adjusted under 35 U.S.C. 154(b) by 0 days.

(21) Appl. No.: 10/153,833

(22) Filed: May 21, 2002

(65) Prior Publication Data

US 2002/0178789 A1 Dec. 5, 2002

Related U.S. Application Data

(62) Division of application No. 09/518,179, filed on Mar. 2, 2000.
(60) Provisional application No. 60/122,688, filed on Mar. 3, 1999, provisional application No. 60/162,683, filed on Nov. 1, 1999, and provisional application No. 60/164,022, filed on Nov. 4, 1999.

(51) Int. Cl.[7] .............................................. G01N 19/10
(52) U.S. Cl. ......................... 73/23.2; 73/23.3; 340/632; 340/603; 340/541; 422/83
(58) Field of Search .............................. 73/23.2, 23.31, 73/23.3, 23.34, 31.05, 1.06, 866.5, 31.06, 29.01, 24.06; 340/632, 603, 541; 422/83; 702/188, 24

(56) References Cited

U.S. PATENT DOCUMENTS

| | | |
|---|---|---|
| 1,455,263 A | 5/1923 | Oberfell ........................ 73/23 |
| 2,743,167 A | 4/1956 | Cherry ........................ 23/255 |
| 3,323,350 A | 6/1967 | Roberts ...................... 73/40.7 |
| 3,415,108 A | 12/1968 | Hubner .......................... 73/23 |
| 3,427,862 A | 2/1969 | Hubner .......................... 73/23 |
| 3,529,459 A | 9/1970 | Vilinstras ....................... 73/23 |
| 3,540,261 A | 11/1970 | Scoggins ....................... 73/28 |
| 4,329,870 A | 5/1982 | Farmer .......................... 73/23 |

(List continued on next page.)

FOREIGN PATENT DOCUMENTS

WO          WO 92/22813          12/1992

*Primary Examiner*—Hezron Williams
*Assistant Examiner*—Rodney Frank
(74) *Attorney, Agent, or Firm*—Foley & Lardner LLP

(57) ABSTRACT

A vapor sensing device that is sufficiently small and lightweight to be handheld, and also modular so as to allow the device to be conveniently adapted for use in sensing the presence and concentration of a wide variety of specified vapors. The device provides these benefits using a sensor module that incorporates a sample chamber and a plurality of sensors located on a chip releasably carried within or adjacent to the sample chamber. Optionally, the sensor module can be configured to be releasably plugged into a receptacle formed in the device. Vapors are directed to pass through the sample chamber, whereupon the sensors provide a distinct combination of electrical signals in response to each. The sensors of the sensor module can take the form of chemically sensitive resistors having resistances that vary according to the identity and concentration of an adjacent vapor. These chemically sensitive resistors can each be connected in series with a reference resistor, between a reference voltage and ground, such that an analog signal is established for each chemically sensitive resistor. The resulting analog signals are supplied to an analog-to-digital converter, to produce corresponding digital signals. These digital signals are appropriately analyzed for vapor identification. The device can then subsequently transmit the digital signals over a computer network, such as the Internet, for analysis at a remote location.

22 Claims, 33 Drawing Sheets

U.S. PATENT DOCUMENTS

| | | | | |
|---|---|---|---|---|
| 4,360,856 A | | 11/1982 | Witthaus | 361/170 |
| 4,660,407 A | * | 4/1987 | Takami et al. | 73/23 |
| 4,670,405 A | | 6/1987 | Stetter et al. | 436/151 |
| 4,761,639 A | | 8/1988 | Pyke et al. | 340/634 |
| 4,818,348 A | | 4/1989 | Stetter | 204/1 T |
| 4,835,372 A | * | 5/1989 | Gombrich et al. | 235/375 |
| 4,864,492 A | | 9/1989 | Blakely-Fogel et al. | 364/200 |
| 4,907,441 A | | 3/1990 | Shurmer | 73/23 |
| 4,922,669 A | | 5/1990 | De Pas et al. | 52/646 |
| 5,025,653 A | | 6/1991 | Schuldt | 73/1 G |
| 5,153,902 A | * | 10/1992 | Buhl et al. | 379/57 |
| 5,218,554 A | * | 6/1993 | Slocum | 364/510 |
| 5,266,944 A | * | 11/1993 | Carroll et al. | 340/825.36 |
| 5,309,777 A | | 5/1994 | Schmitt et al. | 73/866.3 |
| 5,390,530 A | * | 2/1995 | Hosonuma et al. | 73/40 |
| 5,469,369 A | | 11/1995 | Rose-Pehrsson et al. | 364/497 |
| 5,500,854 A | * | 3/1996 | Uotila | 370/17 |
| 5,571,947 A | | 11/1996 | Senn et al. | 73/31.05 |
| 5,579,001 A | * | 11/1996 | Dempsey et al. | 340/870.01 |
| 5,582,797 A | | 12/1996 | Kewley et al. | 422/83 |
| 5,604,299 A | * | 2/1997 | Cobb | 73/31.02 |
| 5,677,476 A | | 10/1997 | McCarthy et al. | 73/29.01 |
| 5,687,734 A | * | 11/1997 | Dempsey et al. | 128/696 |
| 5,708,195 A | * | 1/1998 | Kurisu et al. | 73/40.5 R |
| 5,719,325 A | | 2/1998 | Kiesele et al. | 73/31.06 |
| 5,801,297 A | | 9/1998 | Mifsud et al. | 73/23.34 |
| 5,828,851 A | | 10/1998 | Nixon et al. | 395/285 |
| 5,832,411 A | | 11/1998 | Schatzmann et al. | |
| 5,834,626 A | | 11/1998 | De Castro et al. | 73/23.3 |
| 5,892,950 A | | 4/1999 | Rigori et al. | 395/705 |
| 5,931,913 A | | 8/1999 | Meriwether et al. | 709/227 |
| 6,013,007 A | * | 1/2000 | Root et al. | 482/8 |
| 6,052,737 A | | 4/2000 | Bitton et al. | 709/248 |
| 6,061,753 A | | 5/2000 | Ericson | 710/107 |
| 6,267,000 B1 | * | 7/2001 | Harper et al. | 73/40.5 R |

\* cited by examiner

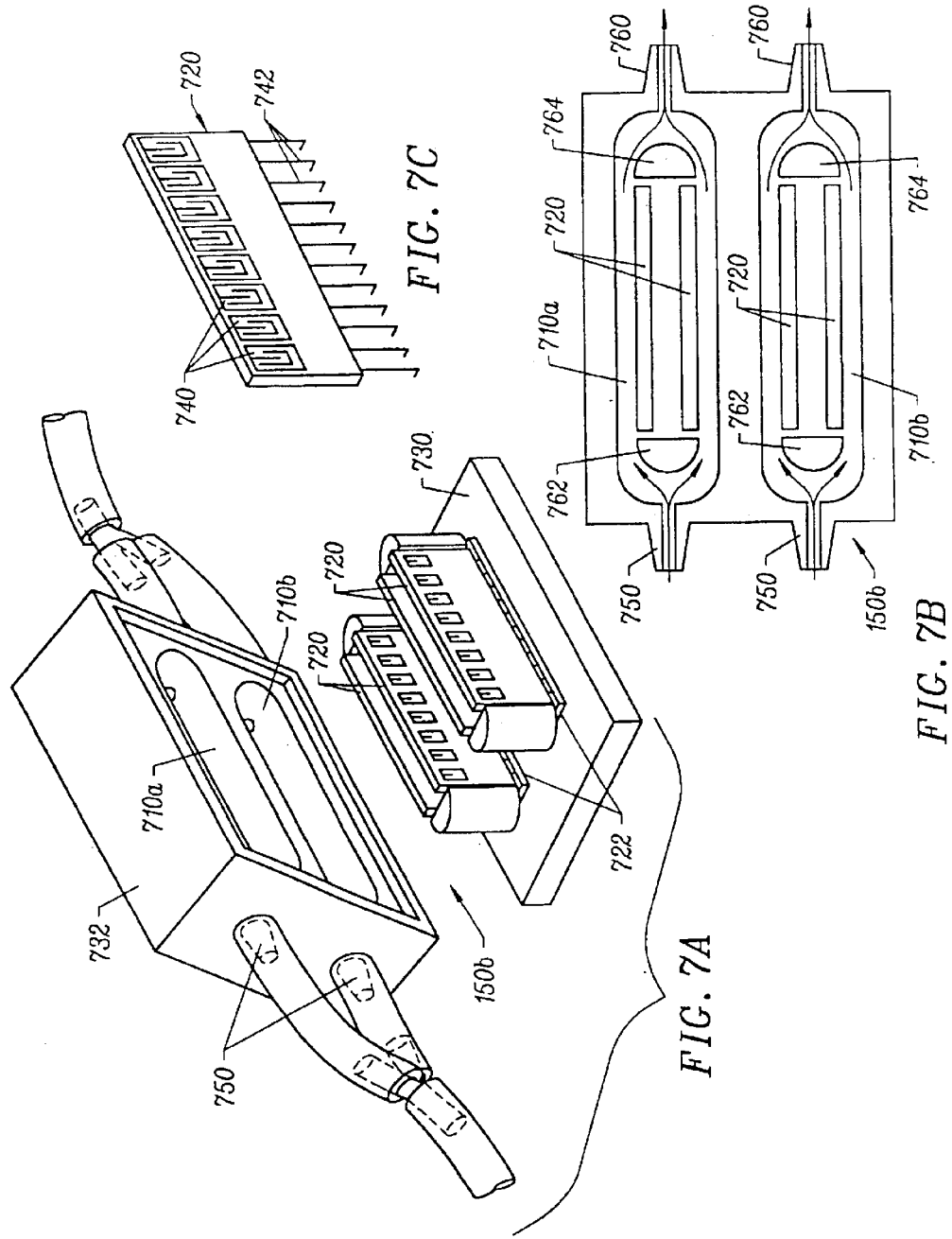

APPARATUS, SYSTEMS AND METHODS FOR DETECTING AND TRANSMITTING SENSORY DATA OVER A COMPUTER NETWORK

CROSS-REFERENCES TO RELATED APPLICATIONS

This application is a divisional of U.S. patent application Ser. No. 09/518,179, filed Mar. 2, 2000, allowed, which application claims the benefit of U.S. Provisional Application Ser. No. 60/122,688, filed Mar. 3, 1999, U.S. application Ser. No. 09/271,873, filed Mar. 18, 1999, U.S. Provisional Application Ser. No. 60/162,683, filed on Nov. 1, 1999 and U.S. Provisional Application Ser. No. 60/164,022, filed on Nov. 4, 1999. All of these applications are incorporated herein by reference in their entirety for all purposes.

BACKGROUND OF THE INVENTION

This invention generally relates to the detection and transmission of sensory data. More particularly, the present invention relates to an apparatus for detecting and transmitting sensory data of analytes from one portable handheld electronic nose (e-nose) to another for analytic purposes.

Techniques and devices for detecting a wide variety of analytes in fluids such as vapors, gases and liquids are well known. As used herein the term "fluid" means gases, vapors and liquids. An electronic nose is an instrument used to detect vapors or chemical analytes in gases, solutions, and solids. In certain instances, the electronic nose is used to simulate a mammalian olfactory system. In general, an electronic nose is a system having an array of sensors that are used in conjunction with pattern-recognition algorithms. Using the combination of chemical sensors, which produce a fingerprint of the vapor or gas, the recognition algorithms can identify and/or quantify the analytes of interest. The electronic nose is thus capable of recognizing unknown chemical analytes, odors, and vapors.

In practice, an electronic nose is presented with a substance such as an odor or vapor, and the sensor converts the input of the substance into a response, such as an electrical response. The response is then compared to known responses that have been stored previously. By comparing the unique chemical signature of an unknown substance to "signatures" of known substances, the unknown analyte can be determined. A variety of sensors can be used in electronic noses that respond to various classes of gases and odors.

A wide variety of commercial applications are available for electronic noses including, but not limited to, environmental toxicology and remediation, biomedicine, such as microorganism classification or detection, material quality control, food and agricultural products monitoring, heavy industrial manufacturing, ambient air monitoring, worker protection, emissions control, and product quality testing. Many of these applications require a portable device because they are located in the field or because they have an inaccessible location for larger laboratory models. Conventionally, most of the electronic noses have been large cumbersome laboratory models incapable of being used in the field and pilot plant applications. If available, a portable or handheld device would provide the portability required for pilot plant and field locations. Unfortunately, the portable chemical detectors that have been developed thus far have many limitations that have kept them from being widely accepted.

For instance, U.S. Pat. No. 5,356,594, which issued to Neel et al., discloses a portable volatile organic monitoring system designed for use in detecting fugitive emissions. The device includes a bar code reader for inventorying the emission site. The device contains a single sensor responsive to ionized gas, however the device only detects the amount (i.e., concentration) of the volatile compound. The device is incapable of identifying the volatile organic compound. Thus, the device is merely a vapor amount logger and not a portable electronic nose. As such, the user is required to know the identity of the vapor being quantitated or this information must be stored elsewhere.

Another example of a portable device is disclosed in U.S. Pat. No. 4,818,348 issued to Stetter. Although this portable device is more sophisticated than the previous example, it still has many limitations. In this instance, the device is capable of identifying a gas or vapor, but the applications are quite limited because of sensor architectural limitations. The sensors making up the array are permanently fixed, and thus, the number and variety of analytes and gases that the device is capable of identifying is quite small. Moreover, because the analyte or vapor being identified interacts with each sensor of the array in a different amount, the reproducibility and stability of the device is quite limited. These limitations affect the device's accuracy in identifying unknowns.

Concurrent with the development of better detection techniques for detecting analytes, there is an emerging need to develop methods and devices to efficiently transmit the collected sensory data for swift analysis. Under some prior customary practices, the sensory data were first captured and then physically transported back to a laboratory or some other designated facility for subsequent analysis. Very often, analyses on these data would not be performed until a substantial period of time had elapsed and consequently their results would not be available for hours, days or even weeks.

Timely transmission and analysis of sensory data for detected analytes have tremendous applications in a variety of areas. There are many instances where it is desirable to obtain results on the analysis of the sensory data in a timely manner. For example, in a hospital/medical environment, it would be greatly beneficial if data collected from a patient can be transmitted quickly to a laboratory to determine the cause of the patient's ailments thereby allowing the doctors to prescribe the necessary treatment without any undue delay. In a similar example, medical and other related data from home monitoring devices can be collected and transmitted swiftly to the appropriate hospitals and/or authorities to allow them to provide better response to home emergencies. In another example, in environments where the presence of certain substances can potentially lead to dangerous conditions, such as a gas leak in a foundry or a home, the swift transmission of sensory data for analysis can very well preempt an impending disaster. Clearly, there are many other situations that one could think of where the efficient transmission of sensory data will generate tremendous benefits. Hence, it would be desirable and beneficial to create a method and system that is capable of timely transmitting sensory data for analysis.

In addition to the need to have timely transmission of sensory data, there is a need to provide easy access to the collective data compiled for the known analytes. The results of any detection analysis are only as good as the data that are available for comparison. At the present time, various analytes have been identified and data therefor have been compiled and stored all over the world. Perhaps, due to the voluminous amount of data that are available, these data are generally not centralized in any one particular depository but are instead separately stored at different facilities. The segregation of these data, therefore, renders a complete and accurate analysis more difficult. Hence, it would be desirable to have a method and system that is capable of providing better access to these available data thereby allowing more accurate analyses to be performed. The present invention fulfills these and other needs by providing a method and system of detecting, transmitting, storing and retrieving sensory information over a computer network.

SUMMARY OF THE INVENTION

The invention relates generally to a sensing apparatus (also referred to as an electronic-nose or e-nose device). The apparatus is compact and, in certain embodiments, configured to be a handheld device. The e-nose device can be used to measure or identify one or more analytes in a medium such as vapor, liquid, gas, solid, and others. Some embodiments of the e-nose device includes at least two sensors (i.e., an array of sensors) and, in some other embodiments, about two to about 200 sensors in an array and preferably about four to about 50 sensors in the array. The device of the present invention can detect sensory data such as physical, chemical, taste, olfaction, optical olfaction, optical parameters or combinations thereof.

The e-nose device is versatile and meets the needs of a wide range of applications in various industries. In certain embodiments, the device is designed as a slim handheld, portable device with various functionalities. In another embodiments, the device is designed as a portable field tool with full functionality. The e-nose device typically includes an internal processor for processing samples and reporting data. Optionally, the device can be coupled to a computer, such as a personal computer, for access to set-up and advanced features and for transfer of data files.

In some embodiments, sections of the e-nose device are disposed within modules that can be installed, swapped, and replaced as necessary. For example, the sensor module, sampling wand or nose, battery pack, filter, electronics, and other components, can be modularized, as described below. This modular design increases utility, enhances performance, reduces cost, and provides additional flexibility and other benefits.

A specific embodiment of the invention provides a handheld sensing apparatus that includes a housing, a sensor module, a sample chamber, and an analyzer. The sensor module and the analyzer mount in the housing. The sensor module includes at least two sensors that provide a distinct response to a particular test sample. The sample chamber is defined by the housing or the sensor module, or both, and incorporates an inlet port and an outlet port. The sensors are located within or adjacent to the sample chamber. The analyzer is configured to analyze a particular response from the sensors and to identify or quantify, based on the particular response, analytes within the test sample.

In a variation of the above embodiment, the housing of the handheld sensing apparatus includes a receptacle, and the sensor module is removably mounted in the receptacle of the housing. In this embodiment, the sensor module can include one or more sensors.

Another specific embodiment of the invention provides a sensor module configured for use with a sensing apparatus. The sensor module is disposed within a housing that defines a receptacle. The sensor module includes a casing, a sample chamber, an inlet port, an outlet port, at least two sensors, and an electrical connector. The casing is sized and configured to be received in the receptacle of the sensing apparatus. The inlet port is configured to be releasably engageable with a port connection of the sensing apparatus when the sensor module is received in the receptacle. The inlet port receives a test sample from the sensing apparatus and directs the test sample to the sample chamber. The outlet port is configured to discharge the test sample from the sample chamber. The sensors are located within or adjacent to the sample chamber and are configured to provide a distinct response when exposed to one or more analytes located within the sample chamber. The electrical connector is configured to be releasably engageable with a mating electrical connector of the sensing apparatus when the sensor module is received in the receptacle. The electrical connector transmits the characteristic signals from the sensors to the sensing apparatus.

Yet another specific embodiment of the invention provides a handheld sensing apparatus for measuring the concentration of one or more analytes within a sample chamber. The sensing apparatus includes two or more chemically sensitive resistors, conditioning circuitry, an analog-to-digital converter (ADC), and an analyzer. Each chemically sensitive resistor has a resistance that varies according to a concentration of one or more analytes within the sample chamber. The conditioning circuitry couples to the chemically sensitive resistors and generates an analog signal indicative of the resistance of the resistors. The ADC couples to the conditioning circuitry and provides a digital signal in response to the analog signal. The analyzer couples to the ADC and determines, based on the digital signal, the identity or concentration of the analyte(s) within the sample chamber.

Yet another embodiment of the invention provides a portable, handheld vapor sensing apparatus that includes a sensor module incorporating a plug-in array of vapor sensors that provide different electrical responses to one or more distinct vapors. The apparatus includes a handheld housing, and the sensor module optionally can be removably mounted in a receptacle formed in the housing. The sensor module defines a sample chamber to which the array of vapor sensors is exposed. The sample chamber incorporates a vapor inlet and a vapor outlet, and a pump is mounted within the housing for directing a vapor sample from the vapor inlet through the sample chamber to the vapor outlet. A monitoring device also is mounted within the housing, for monitoring the electrical responses of the array of vapor sensors and for producing a corresponding plurality of sensor signals. In addition, an analyzer is mounted within the housing for analyzing the plurality of sensor signals and to identify any vapor sample directed through the sample chamber by the pump.

In more detailed features of the invention, the handheld vapor sensing apparatus further includes a controller or processor configured to control the pump either to direct one of a plurality of reference vapors or an unknown vapor sample through the sample chamber. When the controller is controlling the pump to direct one of the plurality of reference vapors through the sample chamber, the monitoring device monitors the electrical responses of the array of vapor sensors to produce a reference signature. Thereafter, when the controller is controlling the pump to direct the unknown vapor sample through the sample chamber, the monitoring device monitors the electrical responses of the array of vapor sensors to produce a vapor sample signature. The analyzer then compares the vapor sample signature with a plurality of reference signatures, to identify the unknown vapor sample.

In other more detailed features of the invention, the sample chamber of the handheld vapor sensing apparatus is defined by the sensor module, alone, and it is sealed from the external environment except for the vapor inlet and the vapor outlet. In addition, each sensor module includes a plurality of first electrical connectors and a plurality of devices of substantially identical size and shape, the devices together carrying the array of vapor sensors and each including a second electrical connector along one edge thereof, for mating engagement with one of the first electrical connectors.

In yet further more detailed features of the invention, the handheld vapor sensing apparatus further includes an electrical circuit that controls the temperature of the array of vapor sensors. In addition, when the sensor module is configured to be removably mounted in the housing receptacle, the module carries an identifier for identifying the vapor sensors it carries, and the monitor further is configured to read the identifier carried by the sensor module received in the receptacle.

In an embodiment, the sensors are implemented with chemically sensitive resistors having resistances that vary according to the concentration of one or more prescribed vapors within the sample chamber. These chemically sensitive resistors are each connected in series with a separate reference resistor, between a reference voltage and ground, such that an analog signal is established for each chemically sensitive resistor. An analog-to-digital converter is responsive to these analog signals and to the reference voltage, to produce digital output signals indicative of the resistances of the various chemically sensitive resistors. A multiplexer can be included for sequentially connecting the various analog output signals to the analog-to-digital converter. In addition, an analyzer is responsive to the digital output signals, to determine the presence and/or concentration of one or more prescribed vapors within the sample chamber.

In yet another embodiment, the e-nose device is used to detect and capture analyte data and subsequently transmit such data over a computer network to a remote location for analysis.

In another embodiment, the present invention provides a system for acquiring sensory data over a wide area network of computers. The system includes a network and a sensory device, such as a handheld sensing device, coupled to the network. The system also includes a communication interface coupled to the sensory device that is configured to communicate with the network.

In still yet another embodiment, the present invention relates to a computer program product for transmitting sensory data in a networked environment. Generally, the networked environment includes a sensory device, such as the handheld sensing device, connected to a remote location by a network. The computer program product includes code for transmitting a sensory data file from a sensory device to a remote location. The computer program product also includes code for receiving the sensory data file at the remote location. The computer program product can also include code for processing the sensory data file at the remote location for a diagnostic purpose. A computer readable storage medium for holding the codes is also included in the computer program product.

In another feature, the present invention provides a use of a handheld sensing apparatus with an interface for communication to the outside world, preferably via a network. A suitable network includes, but is not limited to, a wide area network, a local-area network, an intranet, a worldwide computer network, and the Internet. The communication is preferably the transmission of sensory information including, but not limited to, physical data, chemical data, taste data, olfaction data, optical olfaction data, optical parameters or combinations thereof. In certain aspects, the network comprises wireless components.

Other features and advantages of the present invention should become apparent from the following description of the preferred embodiments, taken in conjunction with the accompanying drawings, which illustrate, by way of example, the principles of the invention.

BRIEF DESCRIPTION OF THE DRAWINGS

FIGS. 7A–7B show a perspective view and a top sectional view, respectively, of an embodiment of a sensor module that includes four sensor devices mounted within two sample chambers;

FIG. 7C shows a perspective view of the sensor array device;

DETAILED DESCRIPTION OF THE INVENTION AND SPECIFIC EMBODIMENTS

Figure 1:
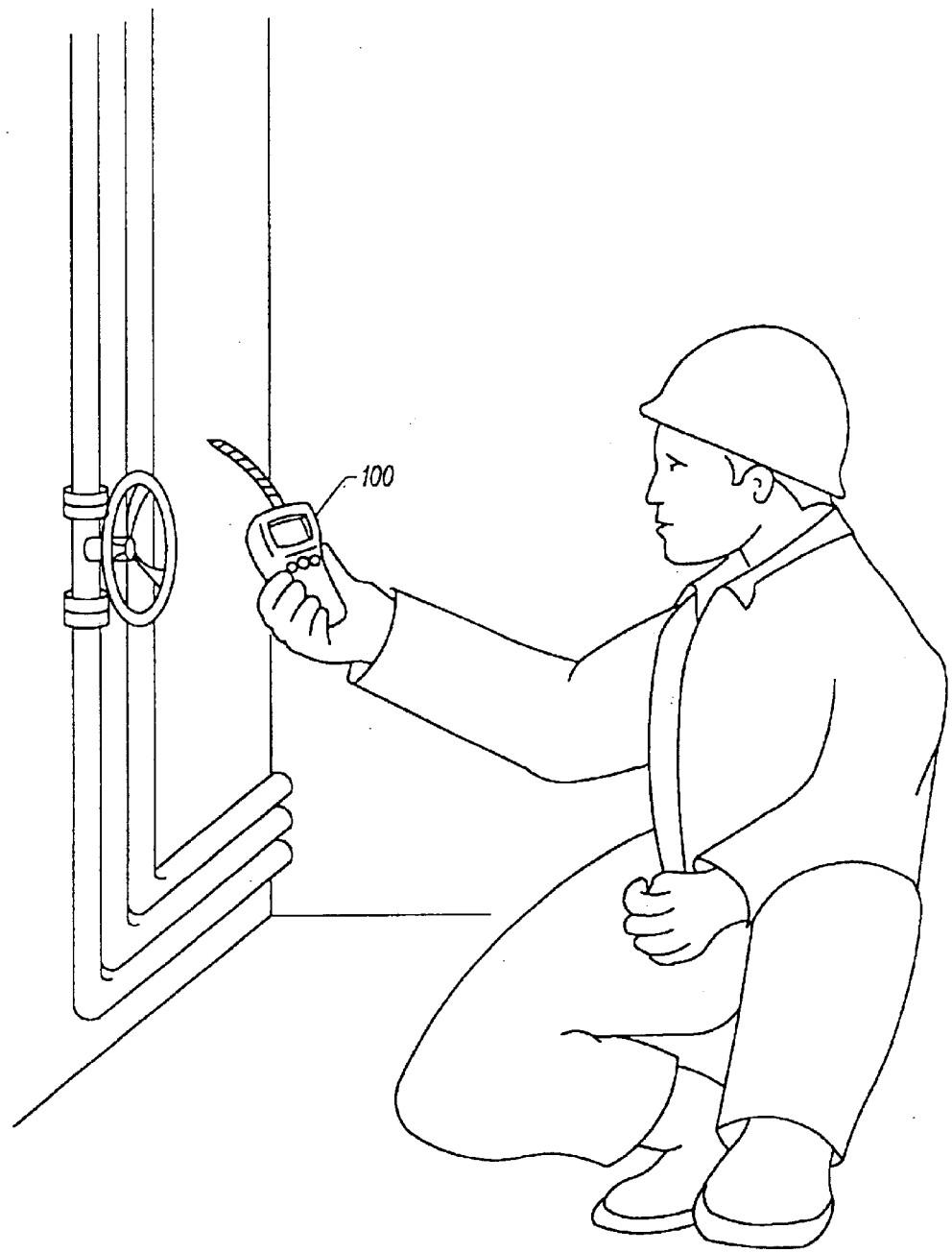
FIG. 1 shows a pictorial view of an operator using an e-nose device.

FIG. 1 shows a pictorial view of an operator using an e-nose device 100. In the embodiment shown in FIG. 1, e-nose device 100 is a portable, handheld instrument for sensing the presence of one or more specified analytes in a particular sample. As use herein, a sample is a unit of a vapor, liquid, solution, gas, solid, or other forms, and mixtures thereof, of a substance being analyzed. Thus, a sample includes chemical analytes, odors, vapors, and others. The sample can comprise a single analyte or a plurality of analytes. In FIG. 1, e-nose device 100 is used for industrial monitoring and detection, i.e., to identify and quantify noxious gas escaping from an industrial valve assembly. E-nose device 100 can also be used for many other applications, as enumerated below.

Figure 2A:
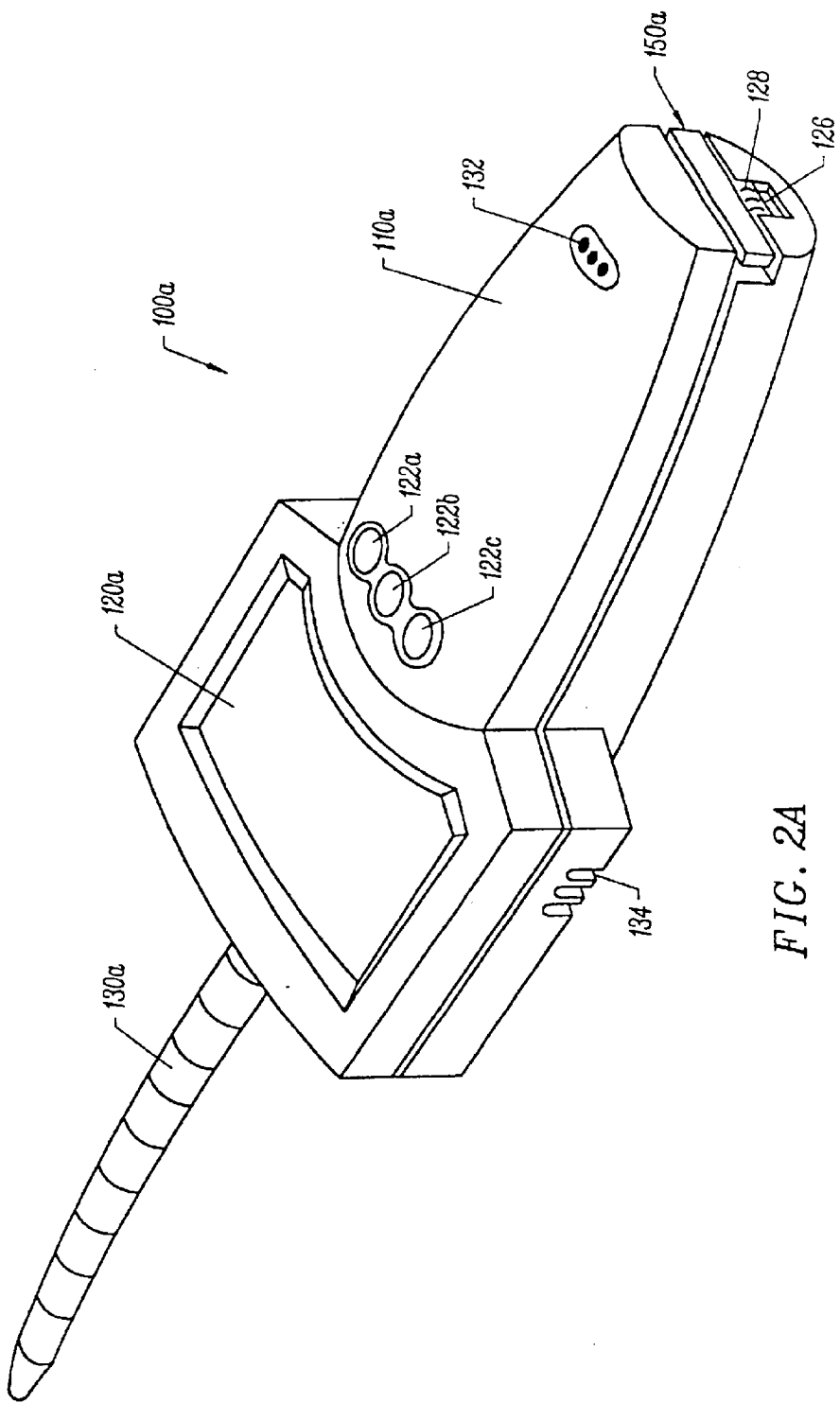
FIGS. 2A and 2B show a top and bottom perspective view, respectively, of an embodiment of an e-nose device.

FIG. 2A shows a top perspective view of an embodiment of an e-nose device 100a. E-nose device 100a includes an elongated housing 110a having a lower end sized to be conveniently grasped and supported by the hand of an operator. A display 120a and several push-button control switches 122a through 122c are located on the housing's topside, for convenient viewing and access by the operator. Push-button switches 122 are used to control the device during its various operating modes. Display 120a displays information about such operating modes and the results of the device's sensing.

A tubular sampling wand 130a and an exhaust port 134 are provided to respectively receive and discharge samples to be analyzed. The sampling wand is also referred to as a nose or snout. A plug-in sensor module 150a is shown installed in its socket located at the base of e-nose device 100a. The operation of sensor module 150a is described in detail below. An electrical connector 126 located at the lower end of housing 110a allows for communication with a host computer, and electrical contacts 128 allow for application of external power that could be used to operate the e-nose device and to recharge the rechargeable battery within the e-nose device.

Figure 2B:
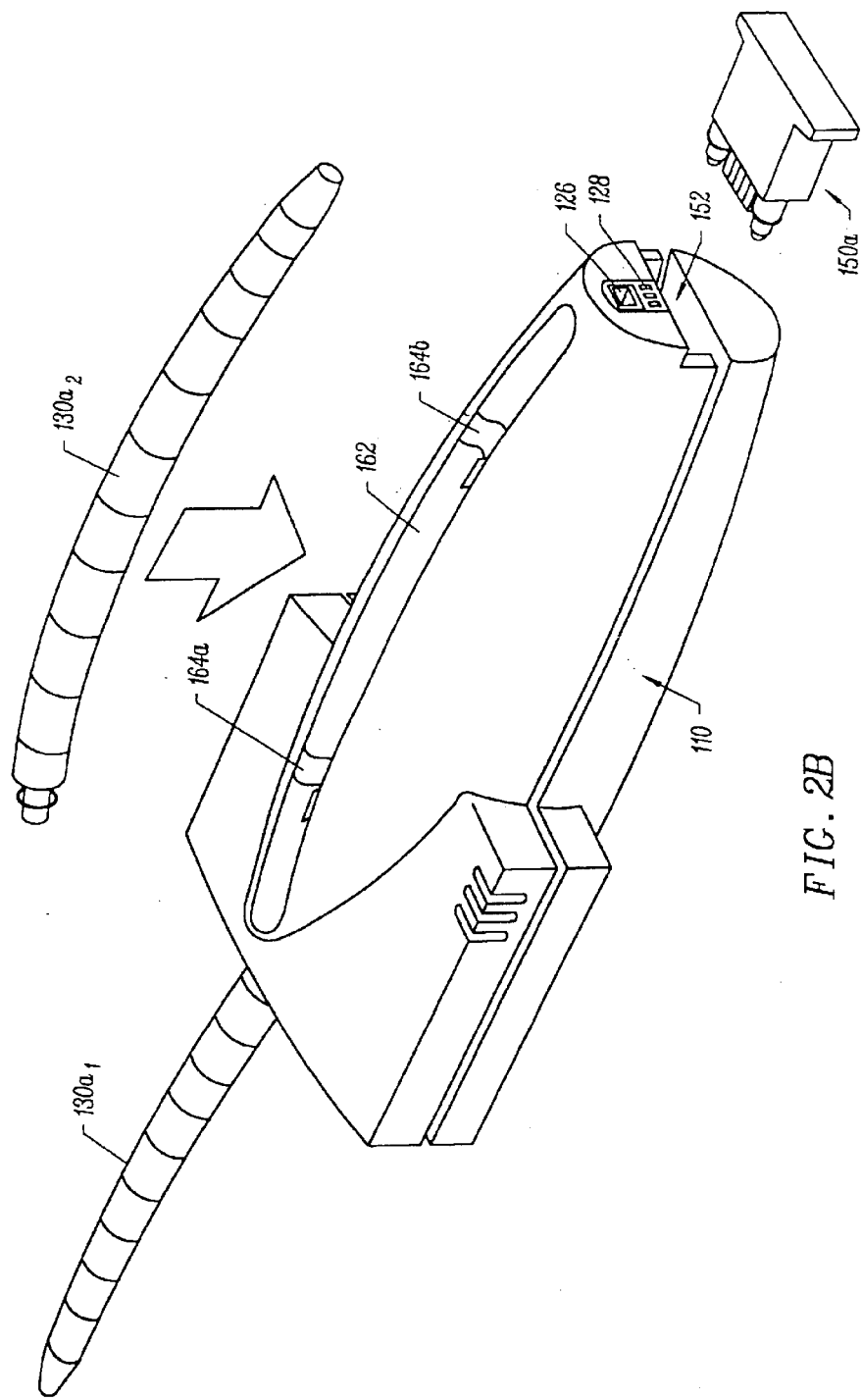

FIG. 2B shows a bottom perspective view of e-nose device 100a. As shown in FIG. 2B, one sampling wand 130a1 is secured in place and a second sampling wand 130a2 is being stored in an elongated recess 162 located on the underside of device 100a. Sampling wand 130a can be stored when not in use and is releasably secured in place by a pair of spring clips 164a and 164b. Plug-in sensor module 150a is shown removed from its socket 152.

Figure 3A:
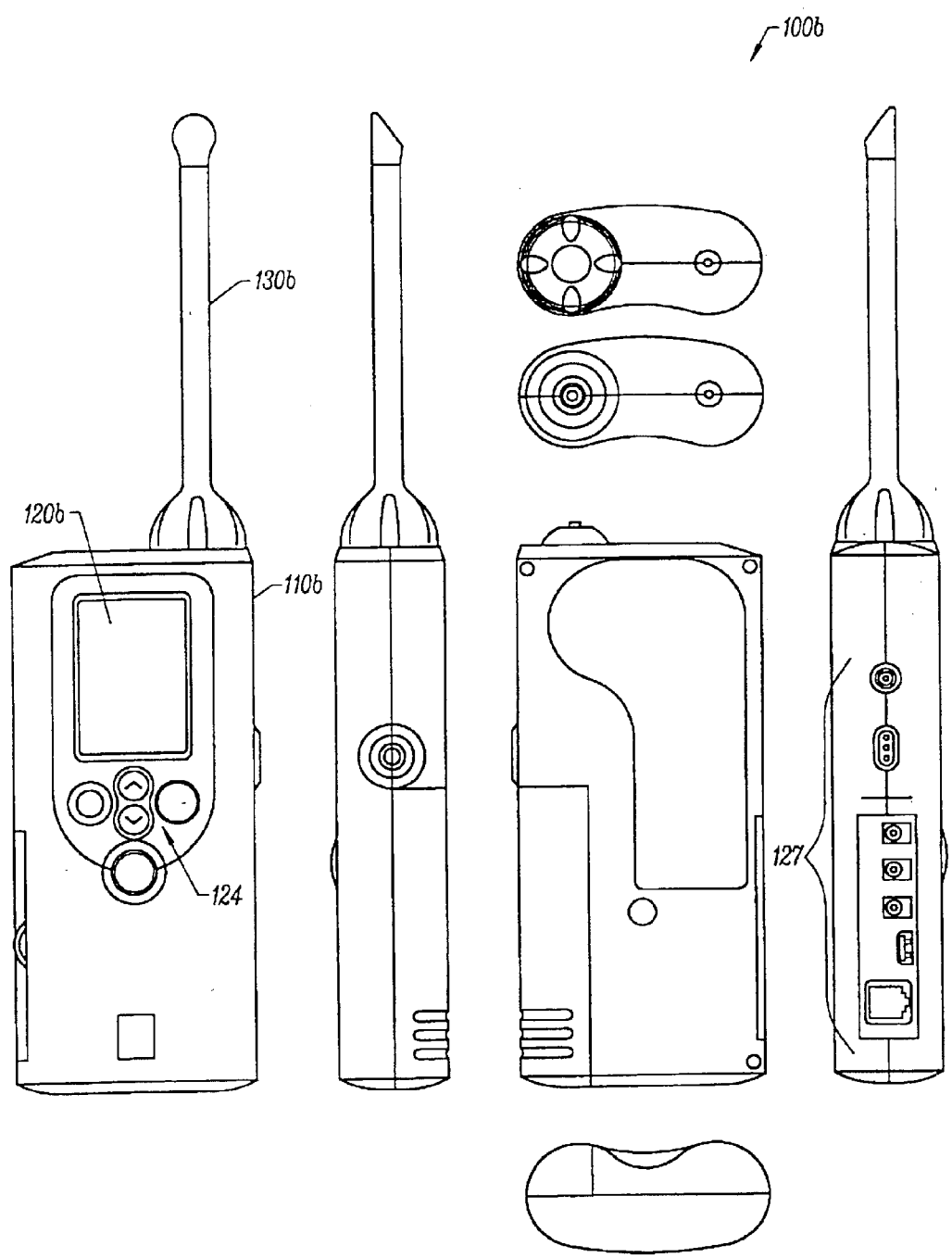
FIG. 3A shows six perspective views of an embodiment of another e-nose device.

FIG. 3A shows six perspective views of an embodiment of another e-nose device 100b. E-nose device 100b includes a nose 130b, a display 120b, and a set of buttons 124. Similar to e-nose device 10a, nose 130b in e-nose device 100b is removably coupled to a housing 110b. A set of connectors 127 allows for interconnection with external devices and systems.

Figure 3B:
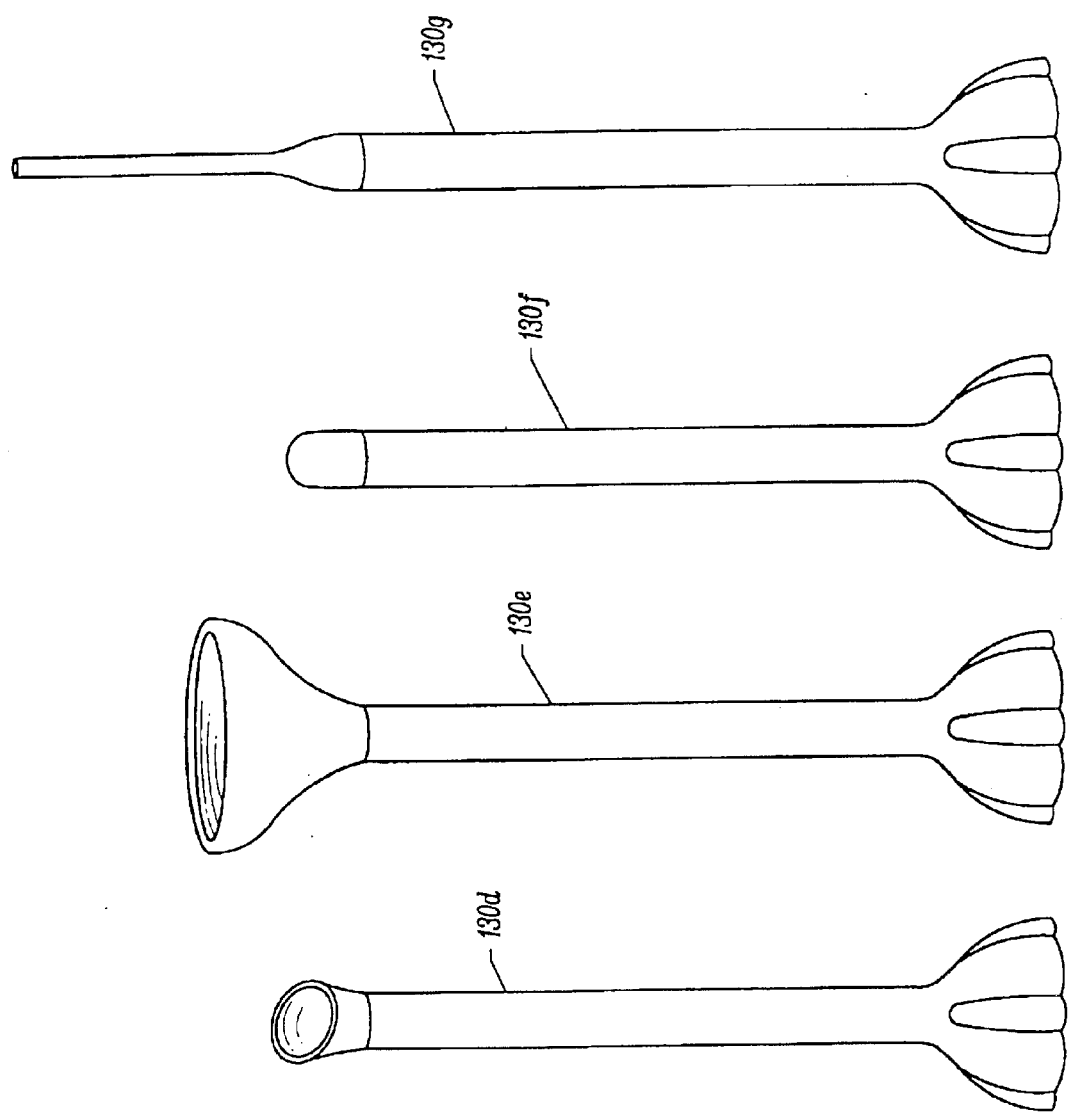
FIG. 3B shows four different embodiments of noses for the e-nose device of FIG. 3A.

FIG. 3B shows four different embodiments of noses 130c through 130f. As these examples illustrate, the noses can be specially dimensioned for improved performance in specific applications.

Figure 4:
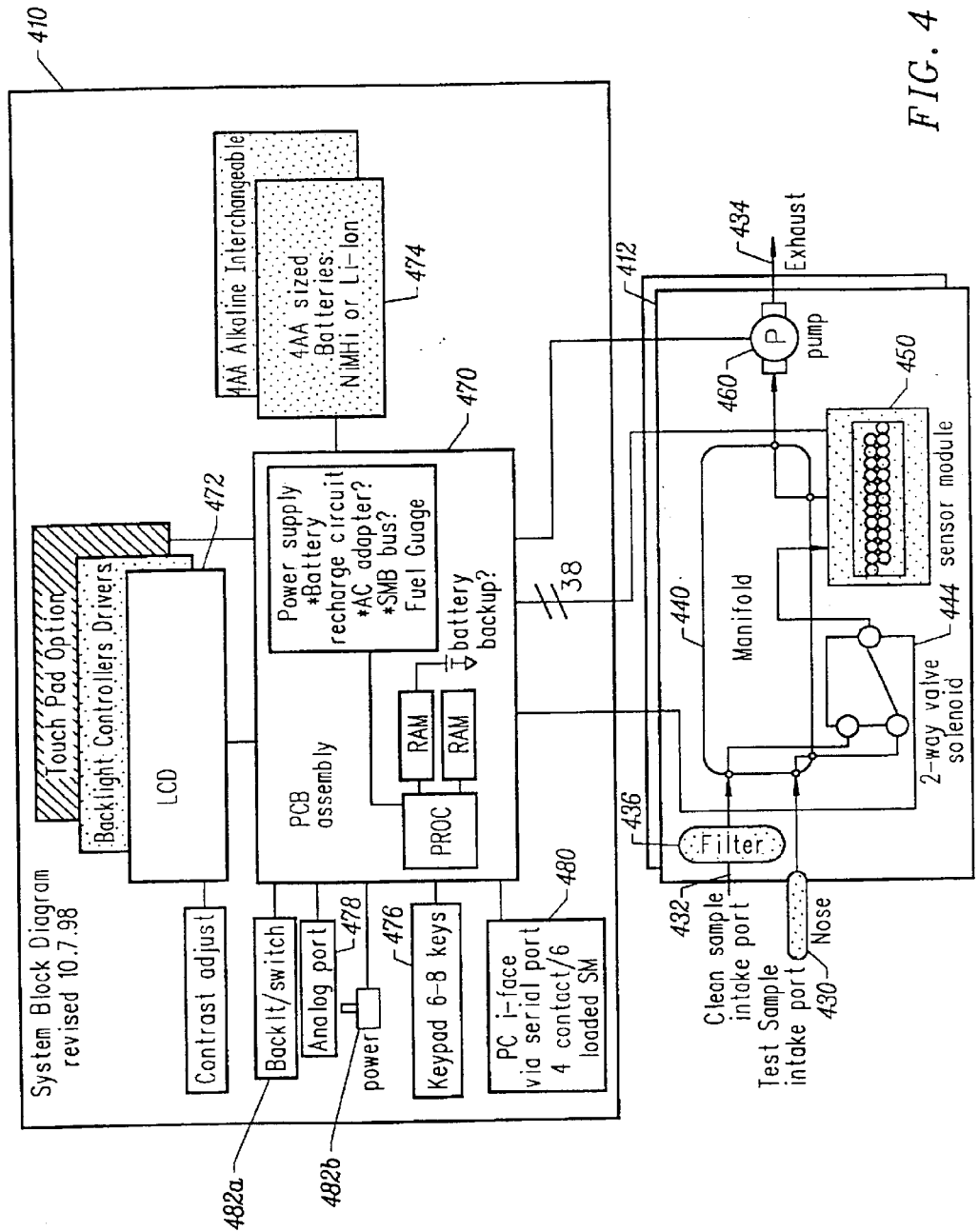
FIG. 4 shows a diagram of an embodiment of the subsystems of the e-nose device.

FIG. 4 shows a diagram of an embodiment of the subsystems of e-nose device 100. The upper half of FIG. 4 shows an electrical subsystem 410 and the lower half shows a (ie., substantially mechanical) subsystem 412 that processes test samples. Within subsystem 412, a test sample is received via a nose 430 and provided to a manifold 440. Similarly, a reference or background sample is received via an intake port 432 and provided through a filter 436 to manifold 440. Filter 436 can be a blank filter, a carbon filter, or others. Manifold 440 directs the test and clean samples to a solenoid 444 that selects one of the samples as the solenoid output. The selected sample is directed through manifold 440 to a sensor module 450. Sensor module 450 includes at least two sensors that detect analytes in the selected sample. Sensor module 450 generates a signal (or a "signature") indicative of the detected analytes and provides this signal to electrical subsystem 410. The selected sample is then provided from sensor module 450, through manifold 440, further through a pump 460, and to an exhaust port 434. Nose 430, intake port 432, exhaust port 434, and sensor module 450 in FIG. 4 generally corresponds to nose 130a, intake port 132, exhaust port 134, and sensor module 150a in FIG. 2A, respectively.

FIG. 4 shows an embodiment of subsystem 412. Many other components and devices (not shown) can also be included in subsystem 412. Further, it is not necessary for all of the components and devices shown in FIG. 4 to be present to practice the present invention. Moreover, the components and devices may be arranged in different configurations than that shown in FIG. 4. For example, pump 460 can be coupled to the output of solenoid 444 instead of exhaust port 434.

As shown by the embodiment in FIG. 4, electrical subsystem 410 includes a PCB assembly 470 that interconnects with a display 472, a battery pack 474, a keypad 476, an analog port 478, an interface 480, and switches 482a and 482b. Display 474 can be a liquid crystal display (LCD) and can include backlight controllers drivers and (optionally) a touchpad. A contrast adjustment mechanism can be provided to adjust display 472. Electrical subsystem 410 is described in further detail below.

Figure 5:
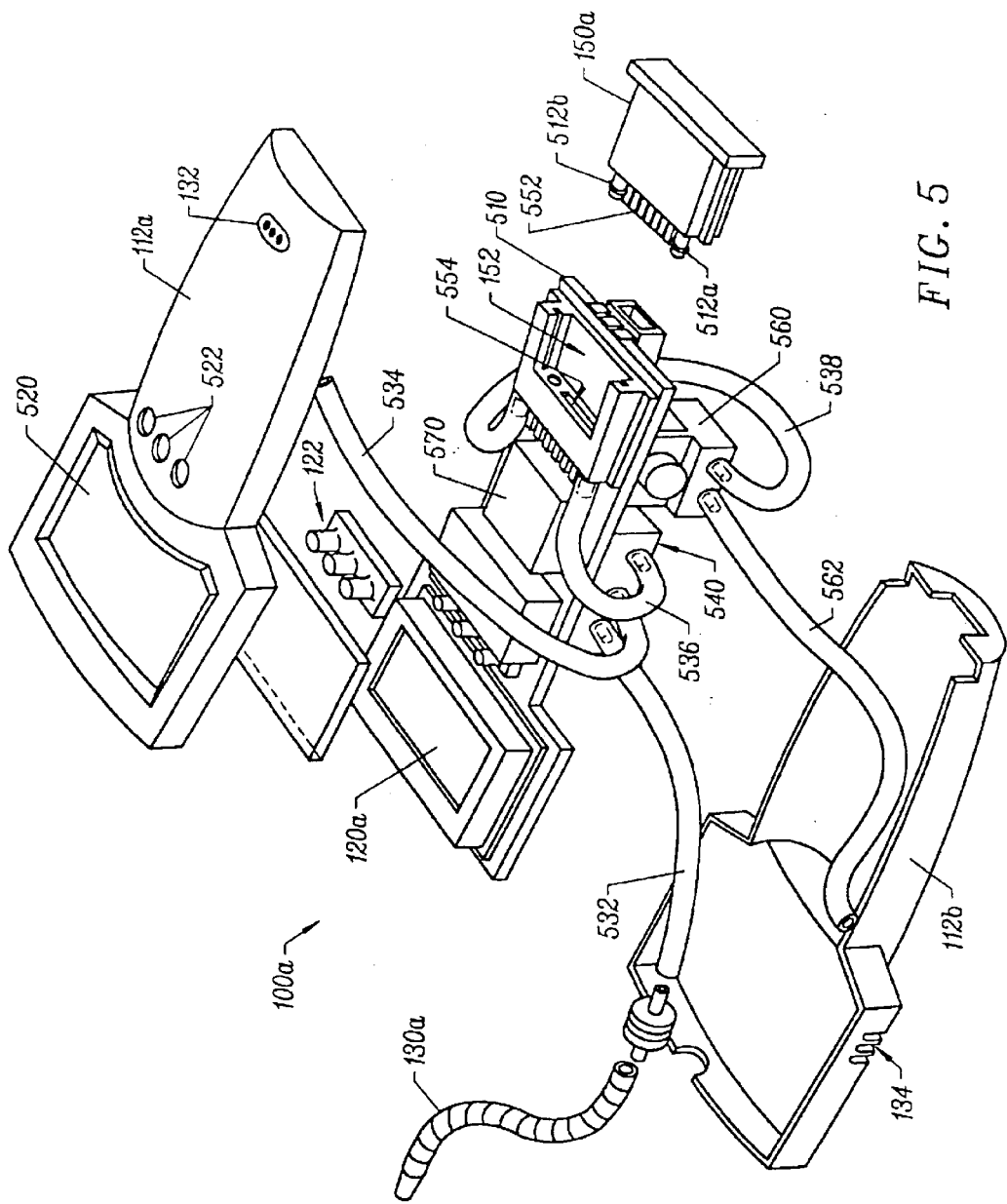
FIG. 5 shows an exploded perspective view of some of the major components of the e-nose device of FIG. 2A.

FIG. 5 shows an exploded perspective view of some of the major components of e-nose device 100a. FIG. 5 also depicts an embodiment of a subsystem 412a. In use, e-nose device 100a is configured to draw in a test sample (i.e., in a vapor, liquid, or gas medium) from a location of interest (i.e., the space adjacent to the valve assembly in FIG. 1) through sampling wand 130a, and to direct this sample through plug-in sensor module 150a installed in socket 152. After passing through sensor module 150a, via ports 512a and 512b, the sample is directed outwardly through exhaust port 134 at the side of the device. At specified times during the device's various operating modes, a reference sample is drawn into the device via intake port 132, directed through sensor module 150a, and discharged through exhaust port 134.

The device's housing 111 a can be formed of molded plastic and includes a lower half 112a and an upper half 112b. Many of the device's internal components are conveniently and efficiently mounted on a printed circuit board (PCB) 510 that extends substantially across the device's interior volume. Display 120a is mounted at the top end of the PCB, where it is visible through an aperture 520 formed in the housing's upper half 112a. The push-button control switches 122a through 122c are mounted below display 120a, in positions where they can extend through correspondingly sized openings 522 formed in the housing's upper half 112a.

A valve assembly 540 mounted on the underside of PCB 510 receives the test sample drawn into e-nose device 100a via sampling wand 130a and the reference sample via intake port 132. The test sample is directed from sampling wand 130a to the valve assembly via a tube 532, and the clean sample is directed from intake port 132 to the valve assembly via a tube 534. Valve assembly 540 is configured to select from one of two sources, coming via either sampling wand 130a or intake port 132. From valve assembly 540, the sample from the selected source is directed via a tube 536 through socket 152 to sensor module 150a, which is located on the top side of the PCB. After analysis by the sensor module, the sample is directed through a tube 538 to a pump 560 located on the underside of the PCB. Finally, the sample is discharged from the device by directing it from pump 560 through a tube 562 to exhaust port 134. Alternatively, pump 560 could be located in the path between valve assembly 540 and sensor module 150a. In an embodiment, the components coming in contact with the sample being processed (including tubes 532, 534, 536, 538, and 562) are formed of an inert or non-corrosive material, such as Teflon, stainless steel, or Teflon-coated metal. Valve assembly 540 in FIG. 5A generally corresponds to manifold 440 and solenoid 444 in FIG. 4, and pump 560 corresponds to pump 460.

In certain aspects, the handheld apparatus of the present invention includes an optional preconcentrator. Advantageously, with certain analytes, such as high vapor pressure analytes, the analyte is concentrated on an absorbent. The preconcentrator can be used to increase the concentration of analytes in the test sample. Preconcentrators are traps composed of an adsorbent material. In use, an adsorbent material attracts molecules from the gas sample that are concentrated on the surface of the adsorbent. Subsequently, the sample is "desorbed" and analyzed. Suitable preconcentrator materials include, but are not limited to, a polymeric adsorbent material, unsilanized glass wool, Teflon or porus glass fiber, and the like. The adsorbent material is packed in a tube, such as a steel tube.

During use, the sample is drawn into the trap that concentrates the components of interest. In some instances, the tube is wrapped with a wire through which current can be applied to heat and thus, desorb the test sample. The sample is thereafter transferred into the module containing the sensors.

The preconcentrator can be disposed in various locations between the sampling wand and the sensor module. In certain aspects, the preconcentrator can be placed in the nozzle of the device or, alternatively, in the manifold or other convenient location upstream of the sensor module. For example, the preconcentrator can be disposed within valve assembly 540, or housed in a unit coupled to the valve assembly (not shown in FIG. 5). Optionally, additional valves can be installed in the device facilitating preconcentration and sensing.

Suitable commercially available adsorbent materials used in preconcentrators include, but are not limited to, Tenax TA, Tenax GR, Carbotrap, Carbopack B and C, Carbotrap C, Carboxen, Carbosieve SIII, Porapak, Spherocarb, and combinations thereof. Preferred adsorbent combinations include, but are not limited to, Tenax GR and Carbopack B; Carbopack B and Carbosieve SIII; and Carbopack C and Carbopack B and Carbosieve SIII or Carboxen 1000. Those skilled in the art will know of other suitable absorbents.

Operation of e-nose device 100 is controlled by a processor disposed within an electronic unit 570 mounted on the topside of PCB 510. Electronic unit 570 further includes one or more memory devices to store program codes, data, and other configuration information. The electronic unit and control of the e-nose device is described in further detail below.

Figure 6A:
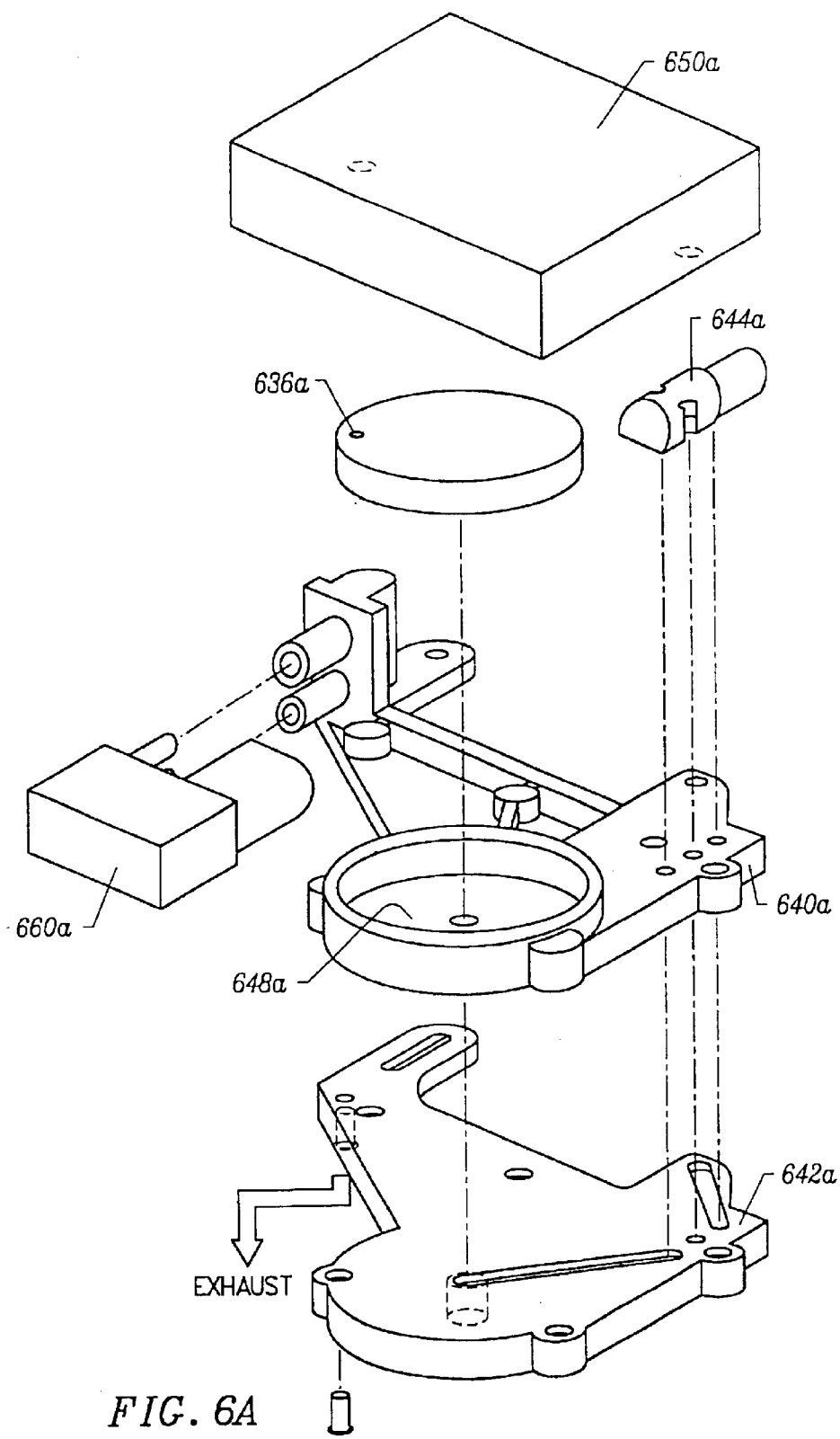
FIGS. 6A and 6B show an exploded perspective view of two embodiments of the mechanical subsystem of the e-nose device.

FIG. 6A shows an exploded perspective view of an embodiment of another subsystem 412b. Subsystem 412b includes a manifold 640a mounted on a manifold seal plate 642a. Manifold 640a includes fittings for mounting a valve (or solenoid) 644a, fittings for mounting a sensor module 650a, and fittings for mounting a pump 660a. The sample is directed between the various sub-assemblies (e.g., valve 644a, sensor module 650a, and pump 660a) via cavities located within manifold 640a and tubes (not shown). Manifold 640a further includes a recessed opening 648a configured to receive a filter 636a.

Figure 6B:
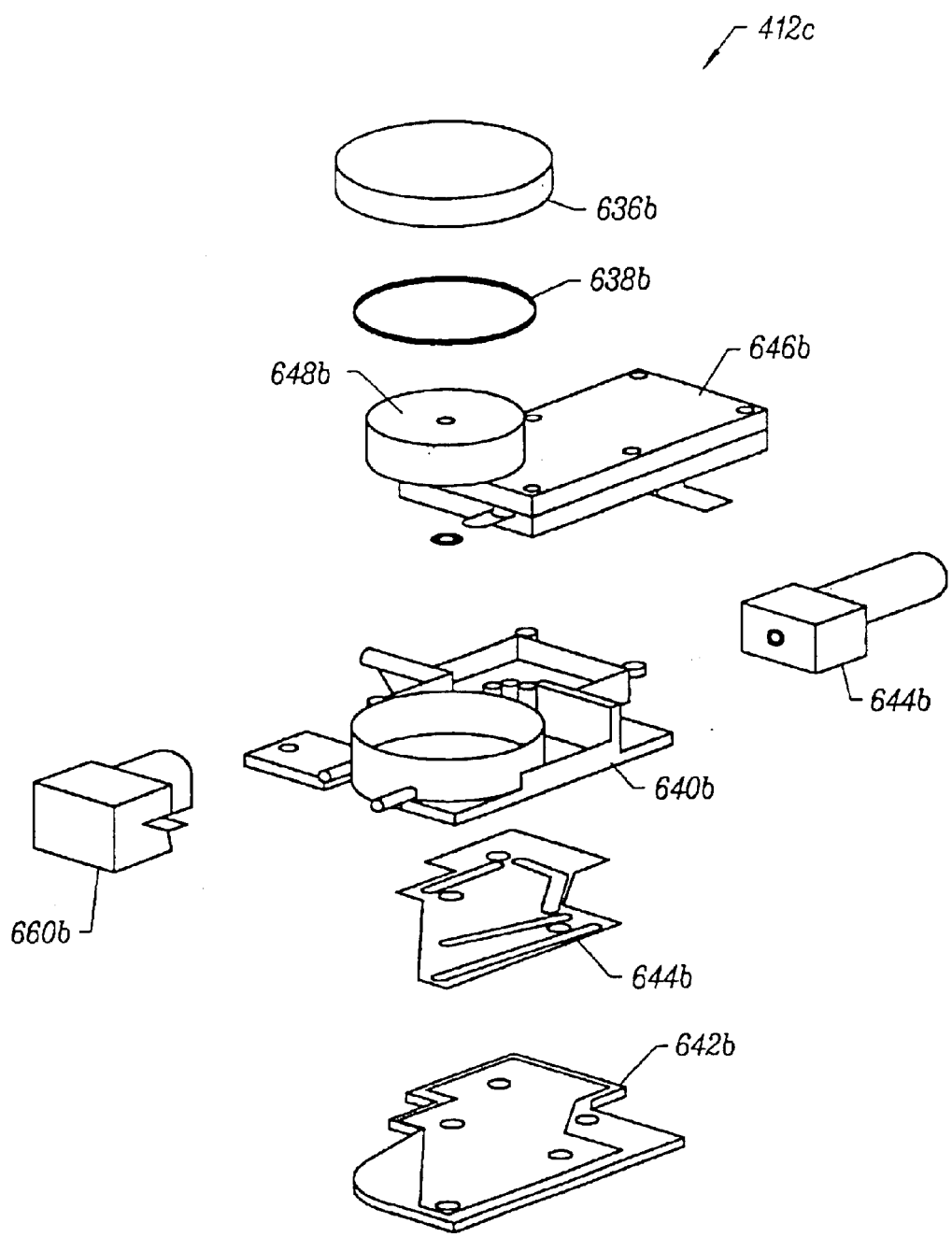

FIG. 6B shows an exploded perspective view of an embodiment of yet another subsystem 412c. Subsystem 412c includes a manifold 640b mounted on a manifold seal plate 642b via a seal plate gasket 644b. Manifold 640b includes fittings for mounting a valve (or solenoid) 644b and fittings for mounting a pump 660b. A filter cartridge 646b mounts on top of manifold 640b and includes a recessed opening 648b configured to receive a filter element. A filter cover 636b encloses recessed opening 648b and an O-ring 638b provides a seal for the filter. The sample is directed between the various sub-assemblies (e.g., valve 644b and pump 660b) via cavities located within manifold 640b and tubes (not shown).

Filter 636, manifold 640, valve 644, sensor module 650, and pump 660 in FIGS. 6A and 6B correspond to filter 436, manifold 440, solenoid 444, sensor module 450, and pump 460 in FIG. 4, respectively.

Figure 6C:
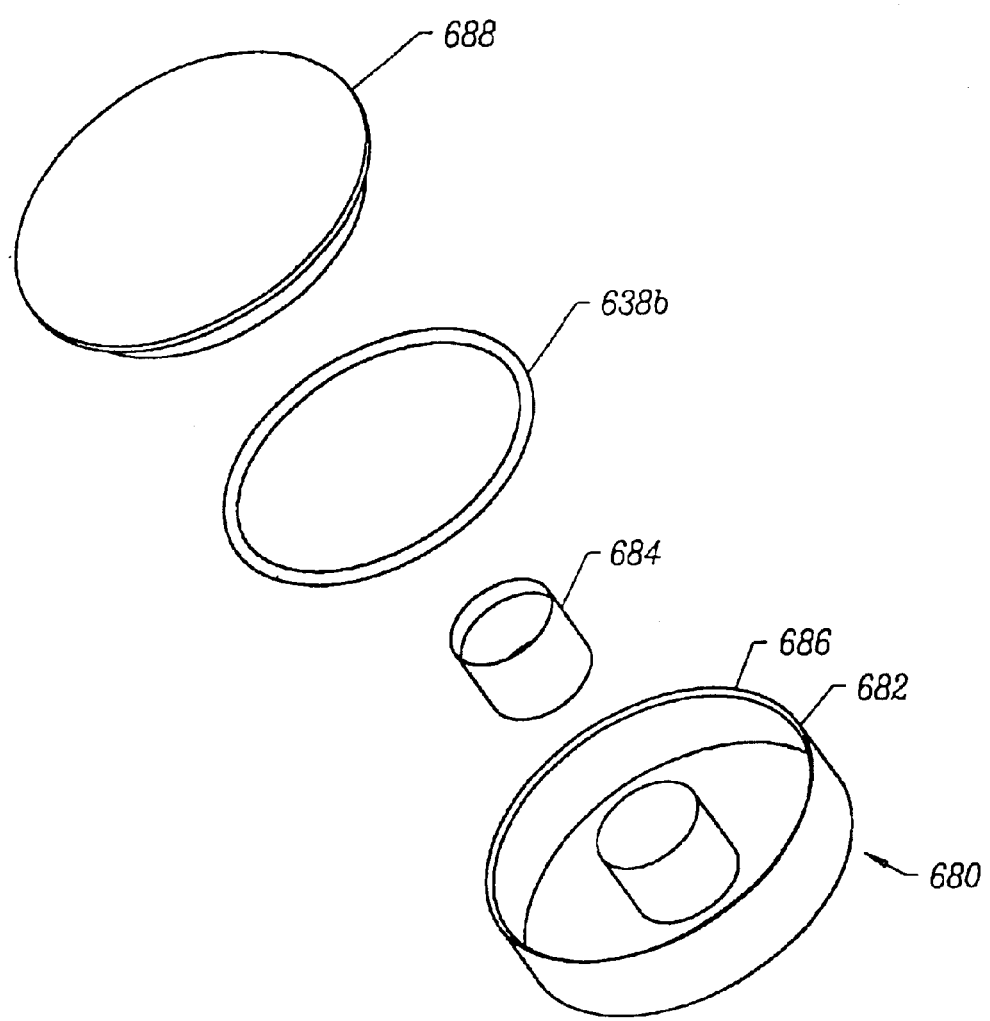
FIG. 6C shows an exploded perspective view of an embodiment of a filter.

FIG. 6C shows an exploded perspective view of an embodiment of a filter. The filter includes a circular base unit 680 having an outer wall 682 and an inner wall 686. A set of small-size openings is disposed within outer wall 682 for drawing in samples into the filter. A inner circular ring 684 covers inner wall 686 that has disposed therein another set of small size openings, for drawing the samples from the filter. A filter material (e.g., charcoal) 688 for filtering the samples is disposed within the space between the outer and inner walls. O-ring 638b is used to seal the filter.

FIGS. 7A–7B show a perspective view and a top sectional view, respectively, of an embodiment of a sensor module 150b that includes four sensor devices mounted within two sample chambers 710a and 710b. In FIGS. 7A and 7B, sensor module 150b is depicted as being configured for non-removable securement to the PCB, but which alternatively could be configured as a plug-in module such as sensor module 150a. In a specific embodiment, sensor module 150b incorporates four plug-in sensor array devices 720, each including eight chemically sensitive sensors 740. Sensor module 150b can include greater or fewer number of sensor array devices, and each sensor array device can include greater or fewer number of sensors. The four sensor array devices 720 are mounted vertically in pairs on a board 730. A cover 732 having a pair of elongated recesses is secured over board 730 so as to define two separate sample chambers 710a and 710b, one for each pair of sensor array devices 720. Sensor array devices 720 are of similar shape and size, and each can be received in any one of the four connectors, or receptacles 722, formed in board 730.

FIG. 7C is a perspective view of one sensor array device 720. In an embodiment, each sensor array device 720 includes an array of eight chemically sensitive sensors 740, each providing a particular characteristic response when exposed to a test sample carrying analytes to be sensed. In an embodiment, the sensors are implemented using chemically sensitive resistors that provide particular resistances when exposed to a test sample. A multi-contact electrical connector 742 is located along the lower edge of sensor array device 720 and is configured for insertion into one of four receptacles 722. Suitable sensor arrays of this kind are disclosed in U.S. Pat. No. 5,571,401, issued in the names of Nathan S. Lewis et al., entitled "Sensor Arrays for Detecting Analytes in Fluids," and incorporated herein by reference. Those of ordinary skill in the art will appreciate that various alternative chemically sensitive sensors or devices could also be used.

As shown in FIG. 7B, the test sample is directed through sensor module 150b from an inlet port 750, through two sample chambers 710a and 710b, and to an outlet port 760. Sensor array devices 720 are arranged such that the test sample moves laterally across the exposed chemically sensitive sensors. Baffles 762 and 764 are located at the respective leading and trailing ends of each sample chamber, to assist in providing an efficient flow pattern, as shown in FIG. 7B.

Figures 8A, 8B:
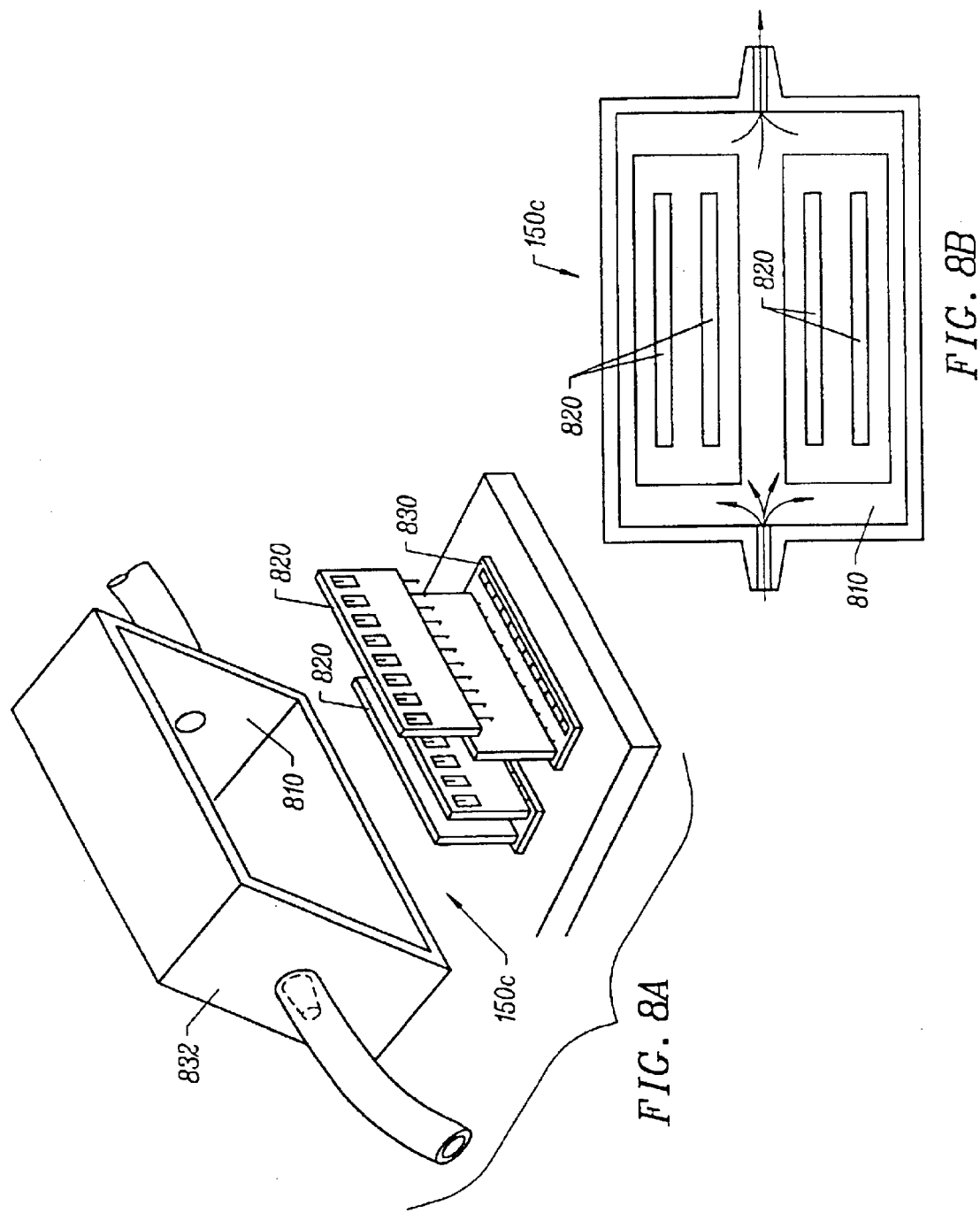
FIGS. 8A and 8B show a perspective view and a top sectional view, respectively, of an embodiment of another sensor module that includes four plug-in sensor devices within a single sample chamber.

FIGS. 8A and 8B show a perspective view and a top sectional view, respectively, of an embodiment of another sensor module 150c that includes four plug-in sensor devices 820 within a single cavity or sample chamber 810. Sample chamber 810 is defined, in part, by a cover 832 that is secured over a board 830. This configuration can be designed to provide a longer dwell time for the test sample within the sample chamber, which can be advantageous in some applications.

Like the chemically sensitive sensors included on sensor array devices 720 in FIGS. 7A and 7B, the chemically sensitive sensors included on sensor array device 820 in FIGS. 8A and 8B can take the form of the arrays disclosed in U.S. Pat. No. 5,571,401. Those of ordinary skill in the art will appreciate that various alternative chemically sensitive sensors or devices could also be used.

Figure 9A:
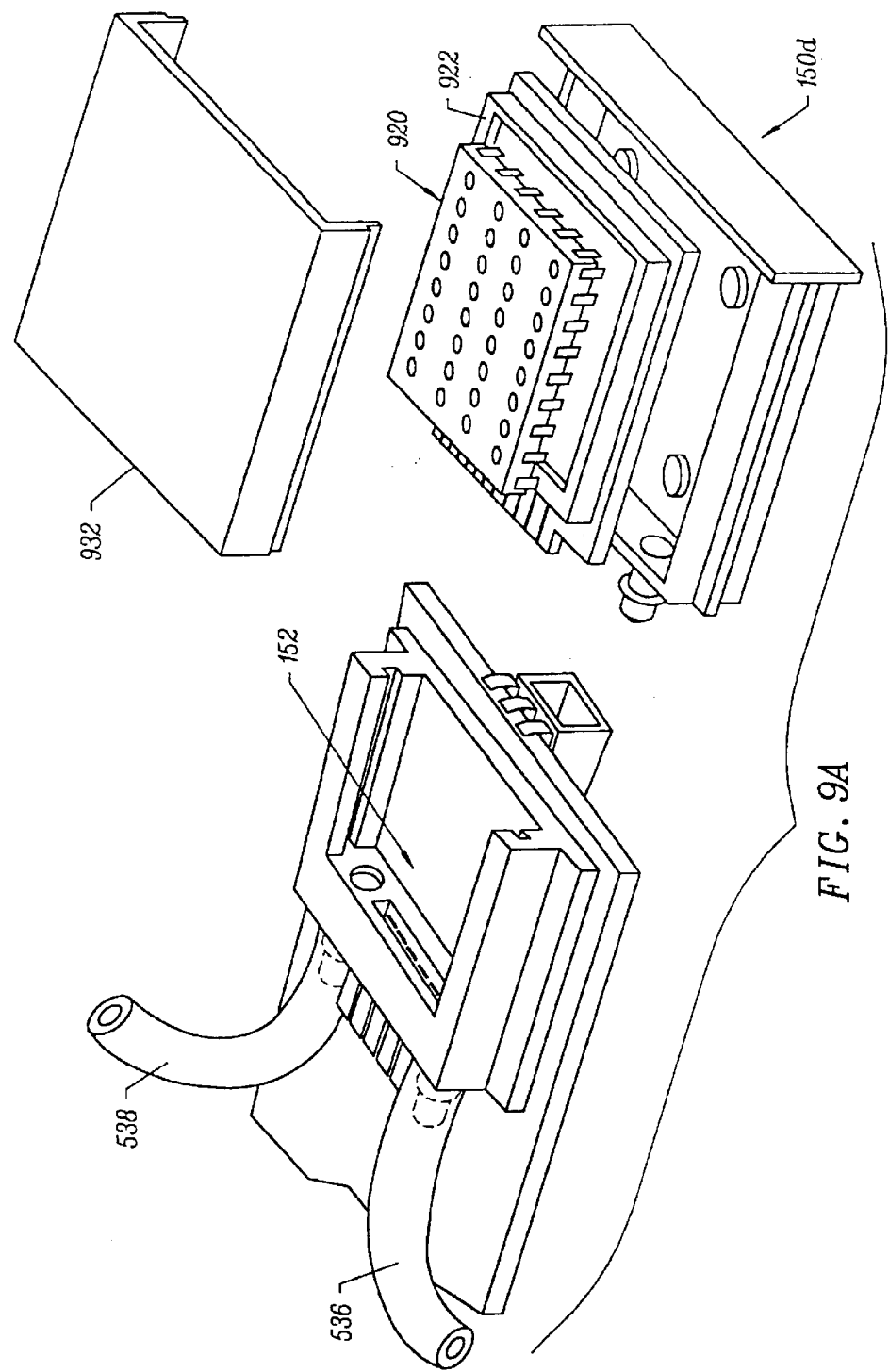
FIGS. 9A through 9C show a perspective view, a side sectional view, and a partial top sectional view, respectively, of an embodiment of a yet another sensor module that includes a single sensor array device.
Figure 9C:
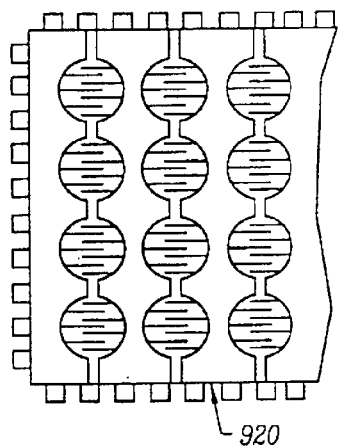
Figure 9B:
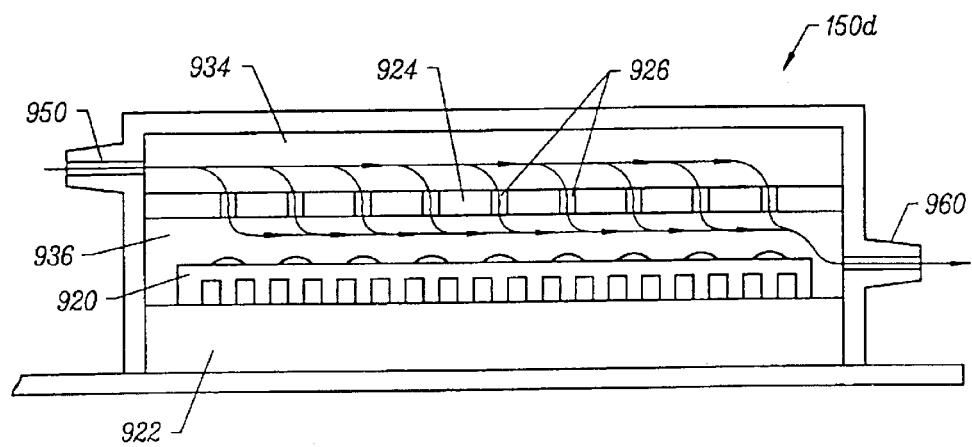

FIGS. 9A and 9B show a perspective view and a side sectional view, respectively, of an embodiment of yet another sensor module 150d that includes a single sensor array device 920. In a specific embodiment, sensor array device 920 includes 32 chemically sensitive sensors arranged in a two-dimensional grid and is mounted in a generally horizontal orientation on a socket 922. Of course, sensor array device 920 can include greater or fewer number of sensors. A screen 924 (see FIGS. 9B and 9C) overlays sensor array device 920 and, in an embodiment, includes a separate opening 926 overlaying each chemically sensitive sensor. Screen 924 is attached to a cover 932, the combination of which defines an upper chamber 934 and a lower chamber 936. As shown in FIG. 9B, the test sample being analyzed is directed from an inlet port 950 to upper chamber 934, and from there through screen 924 to lower chamber 936 where it passes across the chemically sensitive sensors. The test sample then exits through an outlet port 960. Again, it will be appreciated that various alternative chemically sensitive sensors and devices could also be used.

The e-nose device of the invention includes an array of sensors and, in certain instances, the sensors as described in U.S. Pat. No. 5,571,401 are used. Various sensors suitable for detection of analytes include, but are not limited to: surface acoustic wave (SAW) sensors; quartz microbalance sensors; conductive composites; chemiresitors; metal oxide gas sensors, such as tin oxide gas sensors; organic gas sensors; metal oxide field effect transistor (MOSFET); piezoelectric devices; infrared sensors; sintered metal oxide sensors; Pd-gate MOSFET; metal FET structures; metal oxide sensors, such as a Tuguchi gas sensors; phthalocyanine sensors; electrochemical cells; conducting polymer sensors; catalytic gas sensors; fiber optical chemical sensors; organic semiconducting gas sensors; solid electrolyte gas sensors; piezoelectric quartz crystal sensors; and Langmuir-Blodgett film sensors.

In a preferred embodiment, the sensors of the present invention are disclosed in U.S. Pat. No. 5,571,401, incorporated herein by reference. Briefly, the sensors described therein are conducting materials and nonconducting materials arranged in a matrix of conducting and nonconducting regions. The nonconductive material can be a nonconducting polymer such as polystyrene. The conductive material can be a conducting polymer, carbon black, an inorganic conductor and the like. The sensor arrays comprise at least two sensors, typically about 32 sensors, and in certain instances 1000 sensors. The array of sensors can be formed on an integrated circuit using semiconductor technology methods, an example of which is disclosed in PCT patent application Ser. No. WO99/08105, entitled "Techniques and Systems for Analyte Detection," published Feb. 19, 1999, and incorporate herein by reference.

In certain instances, the handheld device of the present invention comprises an array of surface acoustic wave (SAW) sensors, preferably polymer-coated SAW sensors. The SAW device contains up to six and typically about four sensors in the array. Optionally, the device includes a preconcentrator with a heater for desorption of the sample.

Figure 10:
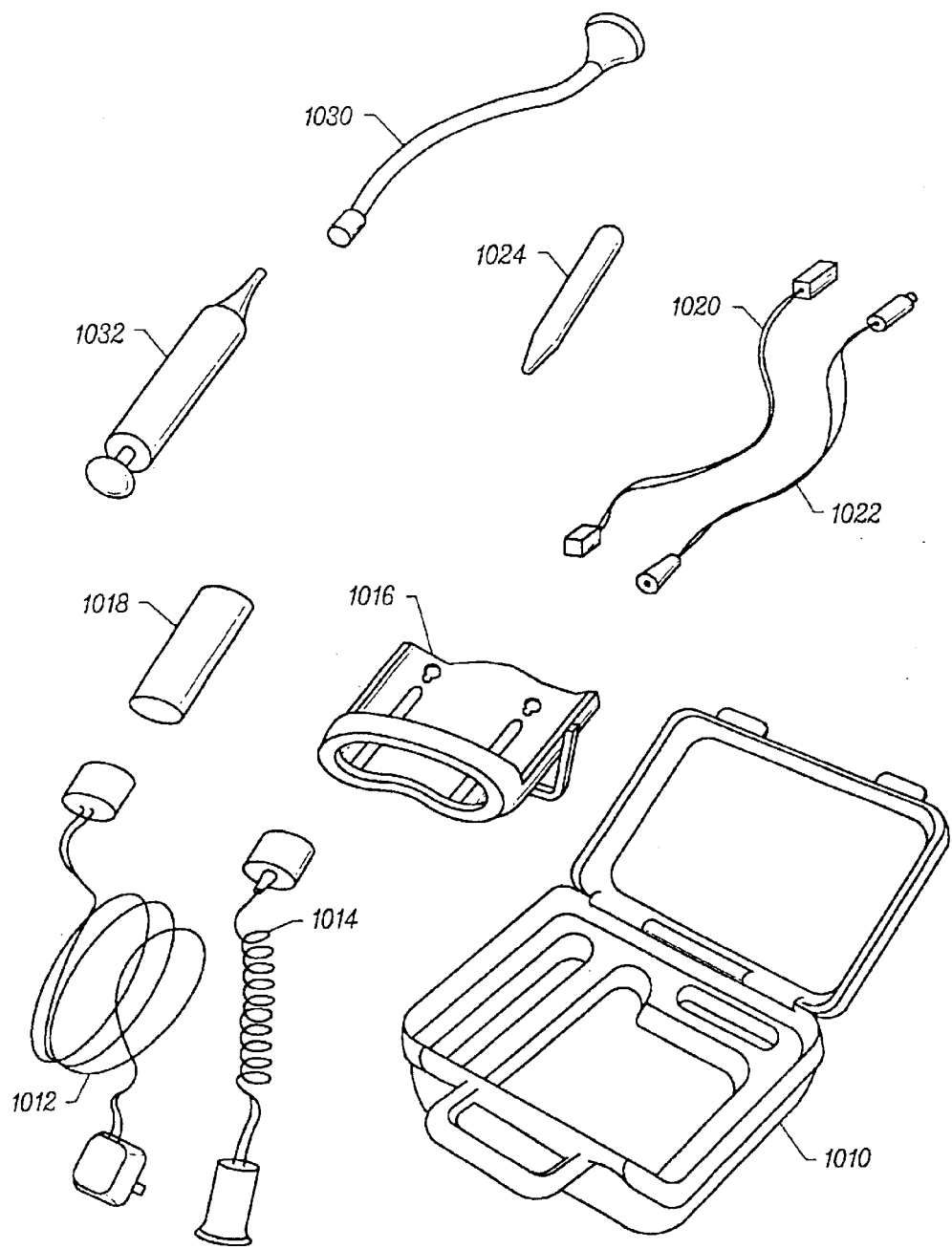
FIG. 10 shows various accessories for the e-nose device.

As will be apparent to those of skill in the art, the sensors making up the array of the present invention can be made up of various sensor types as set forth above. For instance, the sensor array can comprise a conducting/nonconducting regions sensor, a SAW sensor, a metal oxide gas sensor, a conducting polymer sensor, a Langmuir-Blodgett film sensor, and combinations thereof FIG. 10 shows various accessories for the e-nose device. A case 1010 is provided for easy transport of the e-nose device and its accessories. A power cord 1012 and a car cord 1014 can each interconnects the e-nose device to a power source (i.e., a wall socket or car lighter) for recharging a rechargeable battery within the e-nose device. These cords also allow for operation of the e-nose device without the battery. A bracket or stand 1016 holds the e-nose device in the desired position. A (primary or spare) battery 1018 allows the e-nose device to be used without connection to a power source. A serial cable 1020 and an analog cable 1022 are used to interconnect the e-nose device with a personal computer and other test equipment. A stylus 1024 is provided for use with a touchscreen. One or more snouts 1030 can also be provided as spares or for use in a particular set of applications. A sample syringe 1032 can be used for collection of test samples.

Figure 11:
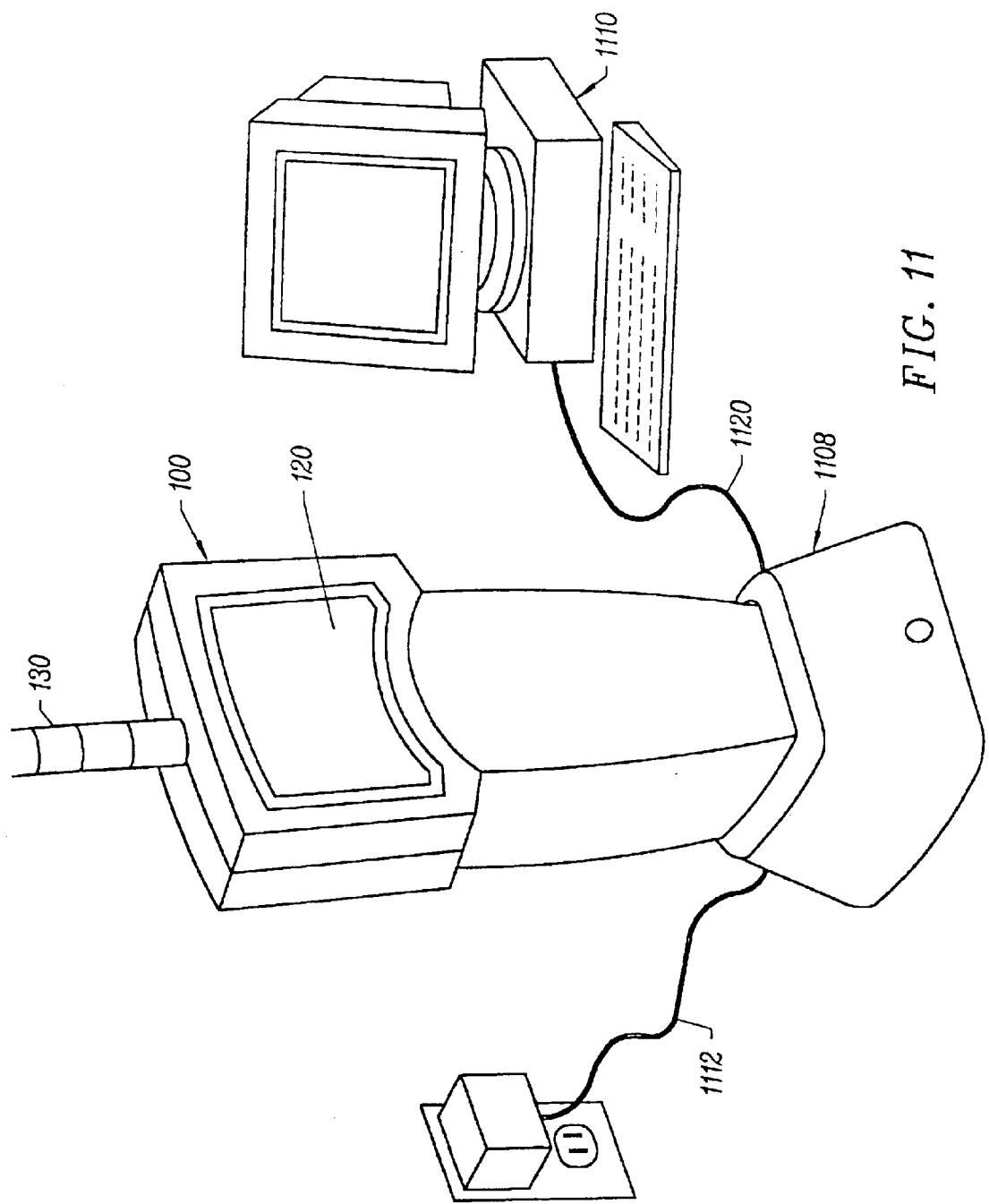
FIG. 11 shows a perspective view of an e-nose device shown mounted vertically in an electrical charging station and coupled to a host computer.

FIG. 11 is a perspective view of e-nose device 100 shown mounted vertically in an electrical charging station 1108 and coupled to a host computer 1110. Charging station 1108 recharges the rechargeable battery of e-nose device 100 via electrical contacts 128 (see FIGS. 2A and 2B). E-nose device 100 is also depicted being coupled to host computer 1110 via a data line 1120. Host computer 1110 can be used to update e-nose device 100 with various information such as the identity of various target vapors to which the device is to be exposed, as well as to retrieve information from the device such as the results of the device's sample analyses.

Figure 12A:
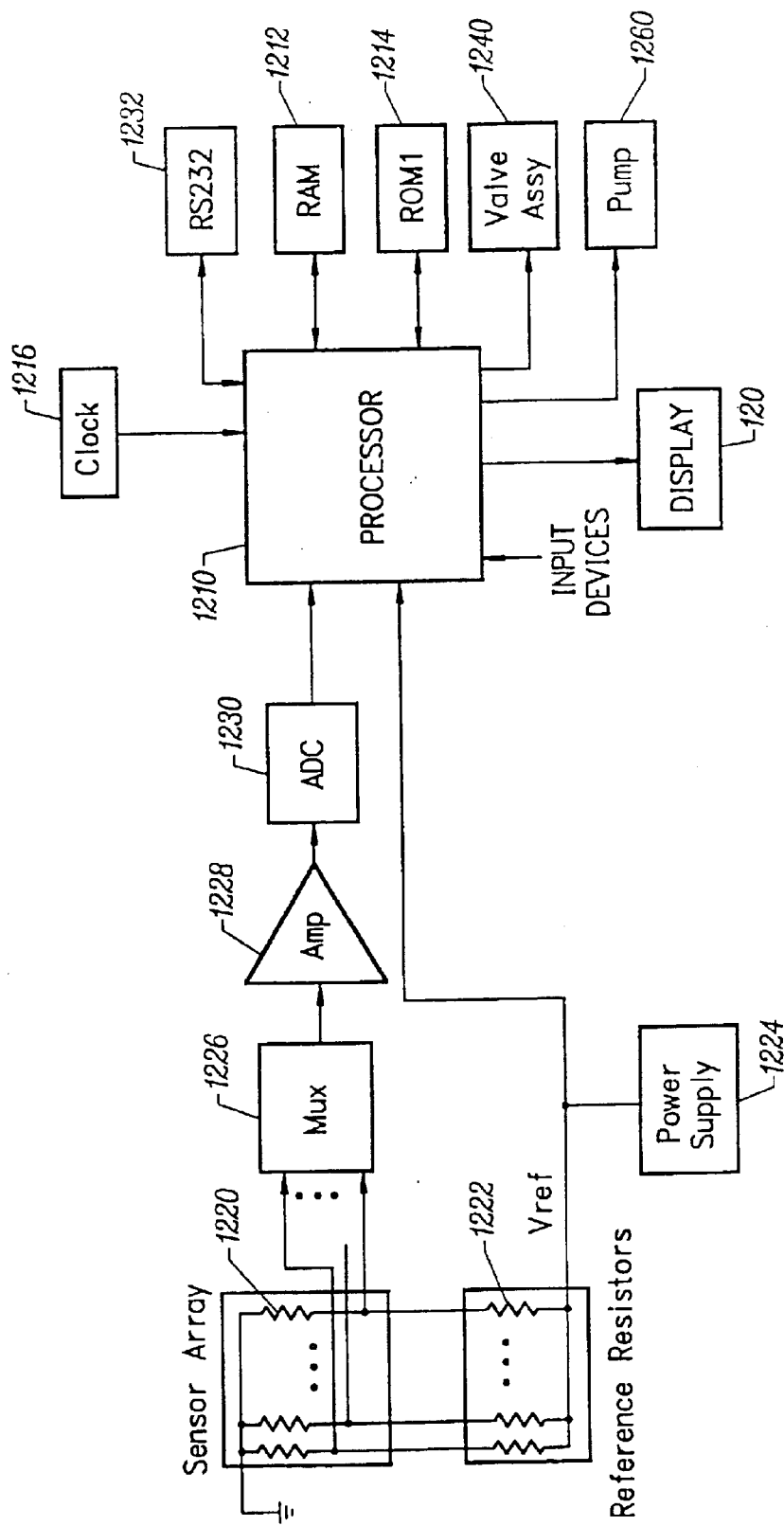
FIG. 12A shows a diagram of an embodiment of the electrical circuitry within the e-nose device.

FIG. 12A is a diagram of an embodiment of the electrical circuitry within e-nose device 100. In an embodiment, the electrical circuitry measures the resistances of the arrays of chemically sensitive resistors mounted on the sensor array devices (see FIGS. 7 through 9) and processes those measurements to identify and quantify the test sample. The circuitry is mounted, in part, on the PCB and includes a processor 1210, a volatile memory (designated as a RAM) 1212, a non-volatile memory (designated as ROM) 1214, and a clock circuit 1216. In the embodiment in which plug-in sensor module 150a is used (see FIGS. 2A and 5), the chemically sensitive resistors are coupled to the electrical circuitry via mating electrical connectors 552a and 552b (see FIG. 5) that are engaged when sensor module 150a is plugged into e-nose device 100a.

The chemically sensitive resistors used to implement the sensors typically have baseline resistance values of greater than 1 kilo-ohm (KΩ). These baseline values can vary as much as ±50% over time. For example, a particular chemically sensitive resistor may have a baseline resistance that varies between 15 KΩ and 45 KΩ. This large resistance variability imposes a challenge on the design of the resistance measurement circuitry. In addition, the ratio of the change in resistance to the initial baseline resistance, or ΔR/R, which is indicative of the concentration of the analytes, can be very small (i.e., on the order of hundreds of parts per million, or 0.01%). This small amount of change, likewise, imposes a challenge on the design of the measurement circuitry. Further, some sensor module embodiments include multiple (e.g., 32) chemically sensitive resistors, and it is desirable to measure the resistance values of all resistors with minimum circuit complexity.

Figure 12C:
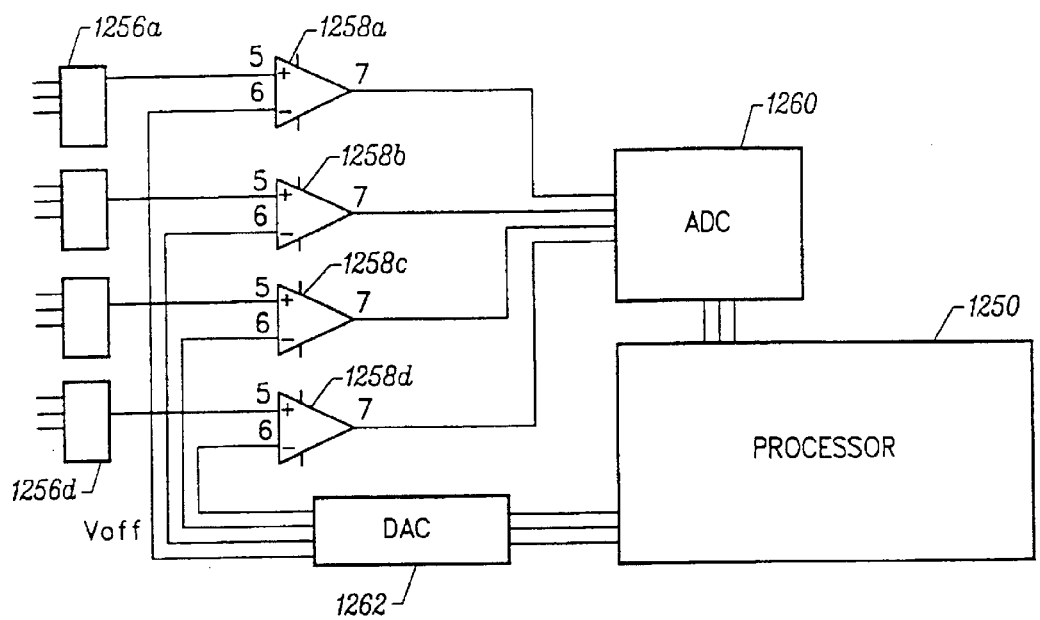
FIG. 12C shows a diagram of another embodiment of the electrical circuitry within the e-nose device.
Figure 12B:
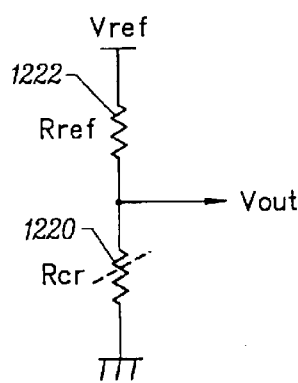
FIG. 12B shows an embodiment of a voltage divider network used to measure the resistance of a chemically sensitive resistor.

FIG. 12B shows an embodiment of a voltage divider network used to measure the resistance of a chemically sensitive resistor 1220. Chemically sensitive resistor (Rch) 1220 is coupled in series to a reference resistor (Rref) 1222 to form a voltage divider network. In an embodiment, a number of voltage divider networks are formed, one network for each chemically sensitive resistor, with each network including a chemically sensitive resistor coupled in series to a corresponding reference resistor. The reference resistors are selected to have a relatively low temperature coefficient. In an alternative embodiment, a single reference resistor is coupled to all chemically sensitive resistors.

Referring back to FIG. 12A, a power supply 1224 supplies a predetermined reference voltage (Vref) to the voltage divider networks such that small changes in the resistance value of each chemically sensitive resistor cause detectable changes in the network output voltage. By appropriately selecting the values of the reference resistors, the electrical current through each chemically sensitive resistor can be limited, for example, to less than about 25 micro amperes (μA). This small amount of current reduces the amount of 1/f noise and improves performance.

The analog voltages from the resistor divider networks are provided through a multiplexer (MUX) 1226 to an analog-to-digital converter (ADC) 1230. MUX 1226 selects, in sequence, the chemically sensitive resistors on the sensor module. Optionally, a low-noise instrumentation amplifier 1228 can be used to amplify the voltage prior to digitization, to improve the ADC's performance and provide increased resolution.

In an embodiment, ADC 1230 is a 22-bit (or higher) delta-sigma ADC having a wide dynamic range. This allows low-noise amplifier 1228 to be set to a fixed gain (i.e., using a single high precision resistor). Commercially available low cost delta-sigma ADCs can reach sampling speeds as fast as about 1 millisecond per channel.

In one implementation, the reference voltage provided by power supply 1224 to the voltage divider networks is also provided to a reference input of ADC 1230. Internally, ADC 1230 compares the divider network output voltages to this reference voltage and generates digitized samples. With this scheme, adverse effects on the divider network output voltages due to variations in the reference voltage are substantially reduced.

The digitized samples from ADC 1230 are provided to processor 1210 for further processing. Processor 1210 also provides timing signals to MUX 1226 and ADC 1230. Timing for the data acquisition can also be provided via a serial link to the ADC and via select lines of the MUX.

FIG. 12C is a diagram of another embodiment of the electrical circuitry within e-nose device 100. In FIG. 12C, four 8-channel multiplexers (MUXes) 1256a through 1256d are provided for added flexibility. The inputs of MUXes 1256 couple to the voltage divider networks (not shown) and the outputs of MUXes 1256a through 1256b couple to four amplifiers 1258a through 1258d, respectively. The select lines for MUXes 1256 are processor controlled. The use of external MUXes offer a low ON resistance and fast switching times. The outputs of amplifiers 1258 couple to four inputs of an ADC 1260.

Each amplifier 1258 is a differential amplifier having a reference (i.e., inverting) input that couples to a digital-to-analog converter (DAC) 1262. The DC offset of the amplifier is controlled by processor 1250 by measuring the offset with ADC 1260 and directing DAC 1262 to provide a proper offset correction voltage. To account for DC drift (i.e., drift in the baseline resistance of the chemically sensitive resistor) the offset can be adjusted prior to actual measurement. Further electrical stability is maintained by placing ADC 1260 on-board and using differential MUXes.

In the embodiments in FIGS. 12A and 12C, amplification is used with the voltage divider networks to achieve detection of PPM changes in resistance values. It can be shown that a gain of 50 provides detection of single PPM increments. In FIG. 12C, amplifiers 1258 also match the signal to be sampled with the full-scale input of ADC 1260. This matching is accomplished by subtracting out the DC component (using DAC 1262) and amplifying the AC component. Thus, it is possible to detect single PPM changes even with a baseline resistance that varies by ±50%.

In FIGS. 12A and 12C, the ADCs used to measure the resistance values can be implemented using a (i.e., 4-channel) high-resolution delta-sigma ADC. The delta-sigma ADC's high resolution coupled with the above-described sensor biasing scheme(s) deliver high flexibility and precision. Presently available delta-sigma ADC can provide 20 bits or more of effective resolution at 10 Hz and 16 bits of resolution at 1000 Hz, with power consumption as low as 1.4 mW.

In an embodiment, the delta-sigma ADC includes differential inputs, programmable amplifiers, on-chip calibration, and serial peripheral interface (SPI) compatibility. In an embodiment, the ADC internal differential MUXes are configured: (1) with respect to ground for increased effective resolution of the measurement, and (2) configured with respect to the reference voltage for high precision measurement, enhanced electronic stability, and to provide a ratiometric measuring mechanism. A status signal from the ADC indicates when the internal digital filter has settled, thus providing an indication to select the next analog channel for digitization.

In FIGS. 12A and 12C, processors 1210 and 1260 can be implemented as an application specific integrated circuit (ASIC), a digital signal processor (DSP), a controller, a microprocessor, or other circuits designed to perform the functions described herein.

One or more memory devices are provided to store program codes, data, and other configuration information, and are mounted adjacent to the processor. Suitable memory devices include a random-access memory (AM), a dynamic RAM (DRAM), a FLASH memory, a read only memory (ROM), a programmable read only memory (PROM), an electrically programmable ROM (EPROM), an electrically erasable and programmable PROM (EEPROM), and other memory technologies. The size of the memories is application dependent, and can be readily expanded as needed.

In an embodiment, the processor executes program codes that coordinate various operations of the e-nose device. The program codes include interaction software that assists the user in selecting the operating modes and methods and to initiate the tests. After the e-nose device performs a test or operation, the user is optionally presented with concise results. In the embodiment in which the device includes a processor and a built-in algorithm, complex functions and capabilities can be provided by the device. In other embodiments in which simplified electronics is provided, complex functions and capabilities of the e-nose device are optionally set up and driven from a host computer using PC based software.

The processors can also be used to provide temperature control for each individual sensor array device in the sensor module. In an implementation, each sensor array device can include a back-side heater. Further, the processor can control the temperature of the sample chambers (e.g., chambers 710a and 710b in FIG. 7A) either by heating or cooling using a suitable thermoelectric device (not shown).

After the processor has collected data representing a set of variable resistance measurements for a particular unknown test sample, it proceeds to correlate that data with data representing a set of previously collected standards stored in memory (i.e., either RAM 1212 or ROM 1214). This comparison facilitates identification of analytes present in the sample chamber and determination of the quantity or concentration of such analytes, as well as detection of temporal changes in such identities and quantities. Various analyses suitable for identifying analytes and quantifying concentration include principal component analysis, Fischer linear analysis, neural networks, genetic algorithms, fuzzy logic, pattern recognition, and other algorithms. After analysis is completed, the resulting information is displayed on display 120 or transmitted to a host computer via interface 1232, or both.

The identification of analytes and the determination of sample concentration can be performed by an "analyzer." As used herein, the analyzer can be a processor (such as processors 1210 and 1260 described above), a DSP processor, a specially designed ASIC, or other circuits designed to performed the analysis functions described herein. The analyzer can also be a general-purpose processor executing program codes written to perform the required analysis functions.

As noted above, to facilitate identification of specified analytes, the variable resistance data from the sensors for a particular unknown test sample can be correlated with a set of previously collected standards stored in memory. These standards can be collected using one of at least two suitable techniques, as described below.

In one technique, a known reference sample is provided to the sample chamber(s). The known sample can be supplied from a small reference cartridge (i.e., located within the e-nose device). The supplies of this reference sample to the sample chambers can be controlled by a compact solenoid valve under the control of the processor. An advantage of using a known reference sample is the ability to control the identity of the reference sample. The cartridge can be replaced periodically.

In another technique, the unknown test sample supplied to the sample chambers can be selectively "scrubbed" by diverting it through a cleansing agent (e.g., charcoal). Again, the diversion of the test sample through the cleansing agent can be controlled by the processor via a compact solenoid valve. An advantage of this variation is that a cartridge is not needed. The cleansing agent can be cleaned periodically, although it may be difficult to ensure that the reference sample is free of all contaminants.

The processors in FIGS. 12A and 12C direct data acquisition, perform digital signal processing, and provide control over serial peripheral devices (via SPI), I/O devices, serial communications (via SCI), and other peripheral devices. Serial peripheral devices that can be controlled by the processors include the ADC and DAC, a 32K external EPROM (with the capability to expand to 64K), a 32K RAM with integrated real time clock and battery back up, a 2×8-character dot matrix display, and others. I/Os that can be controlled include five separate temperature probes (four are amplified through amplifiers and are used for four independent heater control loops utilizing transistors), a humidity probe, two push buttons, a green LED, and others. Serial communications to external devices is provided by the on-board low power RS-232 serial driver.

The processors further control the peripheral devices such as the display, the valve assembly, and the pump. The processors also monitor the input devices (e.g., push button switches 122 in FIG. 2A) and further provides digital communication to a host computer via an interface (e.g., the RS-232 driver) located in the device's housing (e.g., electrical connector 126 in FIG. 2A).

In the embodiment in FIG. 12C, data acquisition includes communication and/or control over the (i.e., 20 bit) delta-sigma ADC, the 4-channel (i.e., 12-bit) DAC 1262, and the four discrete 8-channel high-speed analog MUxes 1256.

The on-board memory (i.e., external RAM) is provided for data logging purposes. In an embodiment, the memory is organized in blocks of 32K×8 bits. In an embodiment, each sample from the ADC is 24 bits and occupies three bytes of memory. Thus, each 32K-byte memory block provides storage for 10,666 samples. If all 32 channels are used for data logging purposes, the memory block provides storage for 333 data points/channel. An internal power supply preserves the data stored in the memory and is designed with a lifetime of over five years. The ADC sampling rate is programmable and the data can be downloaded over the digital RS-232 interface to the host computer.

Communication between the on-board processor and the host computer is available to configure the device and to download data from or to the outside world, in real time or at a later time via a number of communication interfaces including, but not limited to, an RS-232 interface, a parallel port, an universal serial bus (USB), an infrared data link, an optical interface and an RF interface. Serial communications to the outside world are provided by the on-board low power RS-232 serial driver. Communication to the outside world includes, but is not limited to, a network, such as a computer network e.g. the Internet accessible via Ethernet, a wireless Ethernet, a token ring, a modem, etc. A transfer rate of 9600 bits/second can transmit approximately 400 data points/second, and higher transfer rates can be used.

FIGS. 13A through 13G depict an embodiment of suitable flowcharts of the functional steps performed by the e-nose device in implementing the measurement and analysis procedures outlined generally above. These flowcharts show how the e-nose device is initialized and then controlled through its various operating modes. In an embodiment, these operating modes include: 1) a Target mode, in which the device is calibrated by exposing it to samples of known identity, 2) an Identify mode, in which the device is exposed to a samples of unknown identity, and 3) a Purge mode, in which the device is purged of resident samples.

Figure 13A:
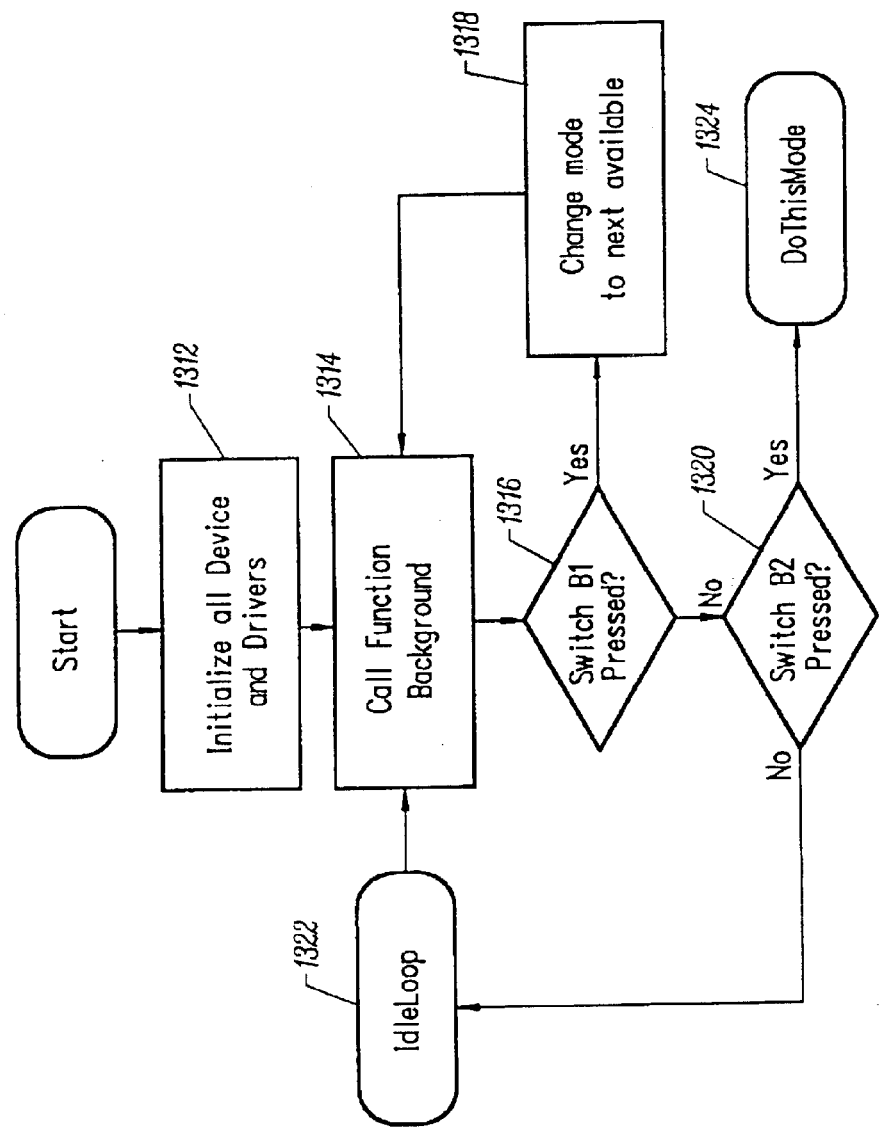
FIGS. 13A through 13G show an embodiment of suitable flowcharts of the functional steps performed by the e-nose device in implementing the measurement and analysis procedures.

FIG. 13A shows a flow diagram of an embodiment of the main program menu of the e-nose device. Initially, the e-nose device's various electronic elements (i.e., the display and various internal data registers) are initialized or reset, at a step 1312. A function background subroutine is then executed, at a step 1314. This subroutine is further described in FIG. 13B.

After executing the function background subroutine, the program proceeds to a step 1316 in which the processor determines whether or not push-button switch B1 (e.g., switch 122a in FIG. 2A) is being pressed. If it is, the program proceeds to a step 1318 in which the device's operating mode increments to the next succeeding mode (i.e., from the Target mode to the Identify mode). Thereafter, the program returns to step 1314 and re-executes the function background subroutine. The incrementing of the device's operating mode continues until it is determined in step 1316 that switch B1 is no longer being pressed.

Figure 13B:
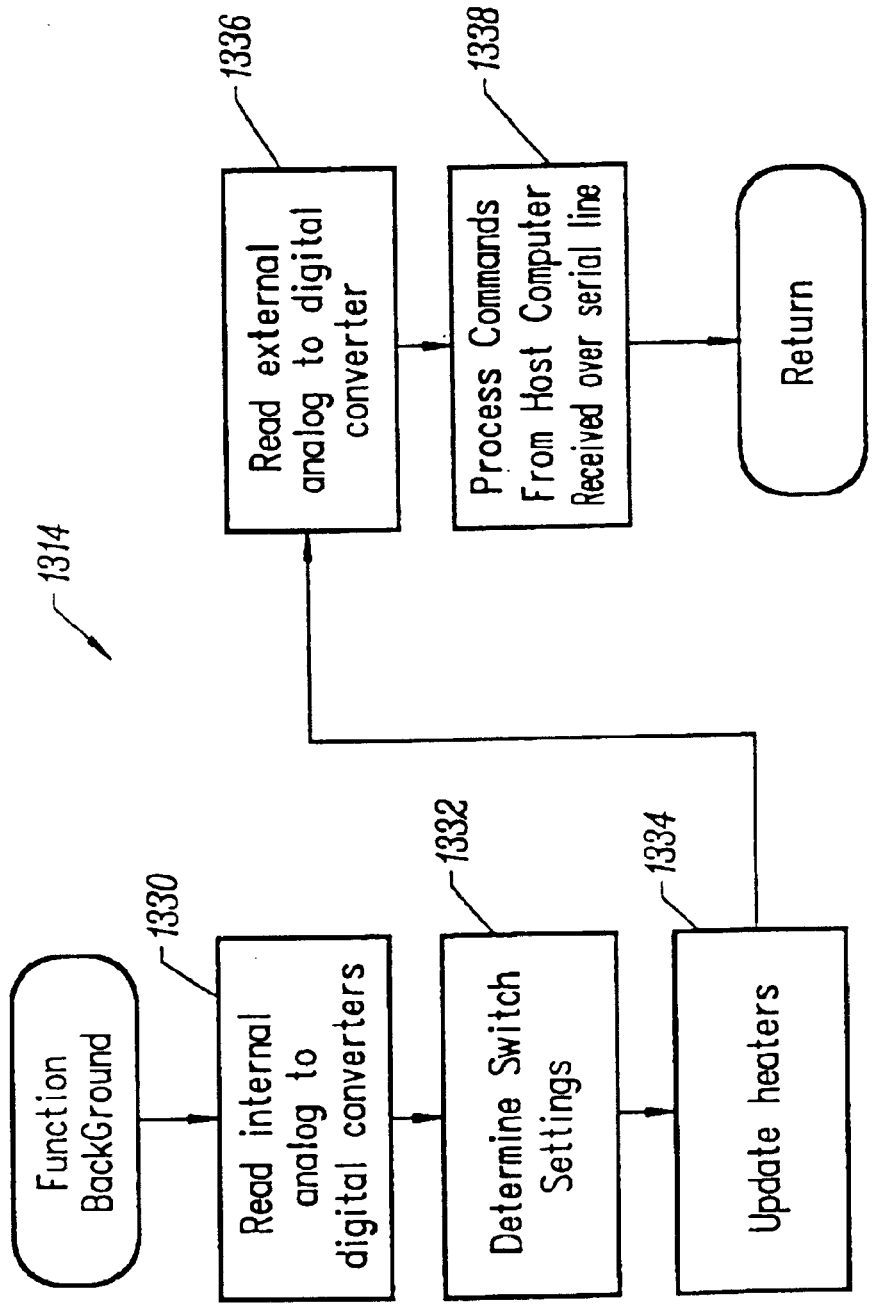

If it is determined at step 1316 that push button B1 is not (or no longer) being pressed, the program proceeds to a step 1320 in which it is determined whether or not push-button switch B2 (e.g., switch 122b in FIG. 2A) is being pressed. If switch B2 is not being pressed, the program returns via an idle loop 1322 to step 1314 and re-executes the function background subroutine. Otherwise, if it is determined at step 1320 that push-button switch B2 is being pressed, the program proceeds to implement the selected operating mode. This is accomplished by the flowchart depicted in FIG. 13C. FIG. 13B shows a flow diagram of an embodiment of the function background subroutine (step 1314). At a step 1330, signals indicative of the measurements and parameters selected by the user (i.e., the temperature and humidity within the sample chambers of the sensor module) are read from the ADCs configured to detect the input devices (also referred to as the internal ADCs). The status of the push-button switches (e.g., switches 122a through 122c FIG. 2A) are determined, at a step 1332, based on the signals from the internal ADCs. The signals controlling the heaters located on various sensor array devices of the sensor module are then updated, at a step 1334. Signals indicative of the measurements of the divider networks, formed by the chemically sensitive resistors and their corresponding reference resistors, are read from the instrumentation ADCs (also referred to as the external ADCs), at a step 1336. Finally, at a step 1338, the processor processes any commands received from the host computer via the serial data line. Such commands can include, for example, programming information about the identity of various reference samples to be supplied to the e-nose device during the target operating mode. The function background subroutine then terminates.

Figure 13C:
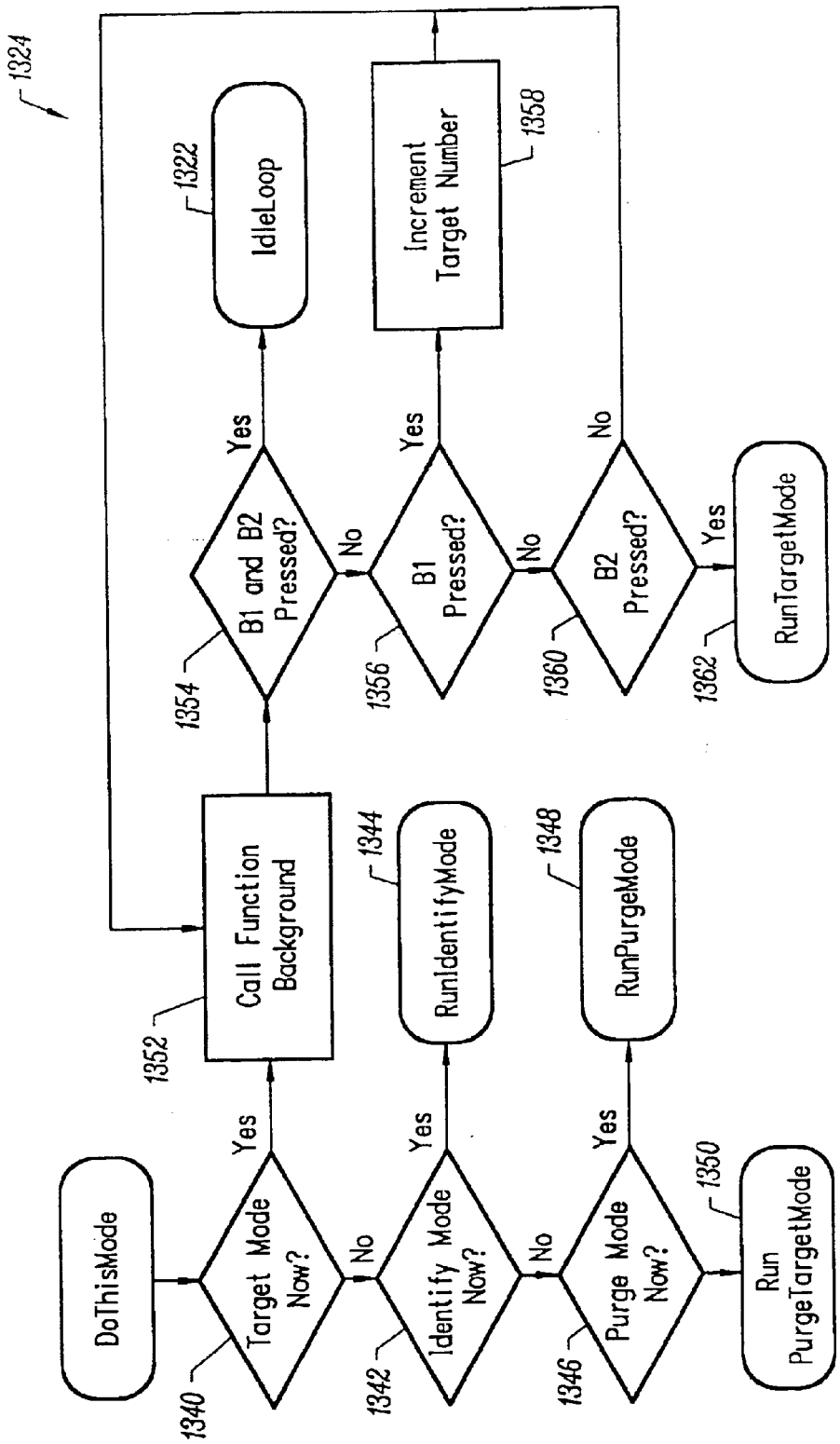

FIG. 13C shows a flow diagram of an embodiment of a subroutine for determining which one of the operating modes to implement. At a step 1340, a determination is made whether or not the selected operating mode is the Target mode. If it is not, a determination is made whether or not the selected operating mode is the Identify mode, at a step 1342. Typically, the Identify mode is selected only after the target mode subroutine has been implemented for all of the designated target samples. If the selected operating mode is the Identify mode, the program executes the identify mode subroutine (depicted in FIG. 13E), at a step 1344.

Otherwise, if the selected operating mode is not the Identify mode, a determination is made whether or not the selected operating mode is the Purge mode, at a step 1346. If it is, the program executes the purge mode subroutine (depicted in FIG. 13F), at a step 1348. Otherwise, the program executes the purge target mode subroutine (depicted in FIG. 13G), at a step 1350. The purge target mode is the default mode.

Back at step 1340, if it is determined that the selected operating mode is the Target mode, the program proceeds to a step 1352 in which the function background subroutine is executed. This provides updated values for the internal and external ADCs, as described above. Thereafter, at a step 1354, it is determined whether or not push-button switches B1 and B2 are being pressed concurrently. If they are, the program does not implement the Target mode and instead returns to the idle loop (step 1322 in FIG. 13A).

Otherwise, if it is determined at step 1354 that both push-button switches B1 and B2 are not being pressed concurrently, the program proceeds to a step 1356 in which it is determined whether or not switch B1 has been pressed. If it has been, the program proceeds to a step 1358 in which the particular target number is incremented. In an embodiment, the e-nose device is configured to measure multiple (e.g., eight) different target samples, and step 1358 enables the operator to select the particular target sample that is to be drawn into the device for measurement. The identity of these target samples previously has been loaded into the device from the host computer. Thereafter, the program returns to the step 1352 to execute the function background subroutine. Each time it is determined that switch B1 has been pressed, the program cycles through this loop, incrementing through the preloaded complement of target samples.

If it is determined at step 1356 that switch B1 has not been pressed, the program proceeds to a step 1360 in which it is determined whether or not switch B2 has been pressed. If it has not, the program returns to step 1352 to execute the function background subroutine. Otherwise, if it is determined in step 1360 that switch B2 has just been pressed, the program proceeds to implement the target mode subroutine (depicted in FIG. 13D), at a step 1362.

Figure 13D:
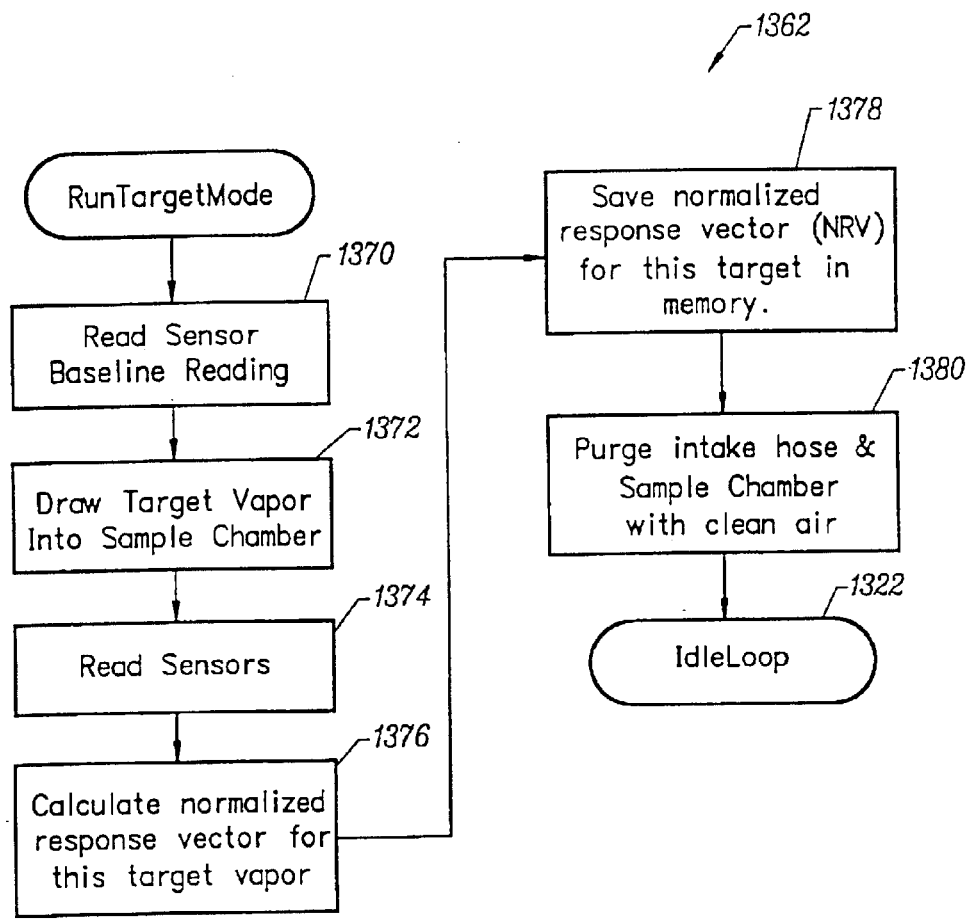

FIG. 13D shows a flow diagram of an embodiment of the target mode subroutine. At a step 1370, the most recently updated set of measurements from the external ADC is retrieved. These measurements represent the baseline resistance values of the 32 chemically sensitive resistors of the sensor module. Next, the pump is conditioned to draw the designated target sample into the sensor module's sample chamber(s), at a step 1372. A new set of measurements is then retrieved from the external ADC, at a step 1374. This new set of measurements indicates the resistance values of the 32 chemically sensitive resistors as they respond to the target sample that has been drawn in the sample chamber(s).

At a step 1376, the 32 resistance measurements (i.e., the "response vector") for this particular target vapor are normalized. In an embodiment, this normalization set the sum of all 32 measurements equal to a value of $1\times10^6$. The normalized response vector for this target sample then is stored in memory, at a step 1378. Finally, at a step 1380, the pump and valve assembly are configured to draw clean air into the sample chamber(s). The target mode subroutine then terminates, and the program returns to the idle loop (step 1322 in FIG. 13A).

Figure 13E:
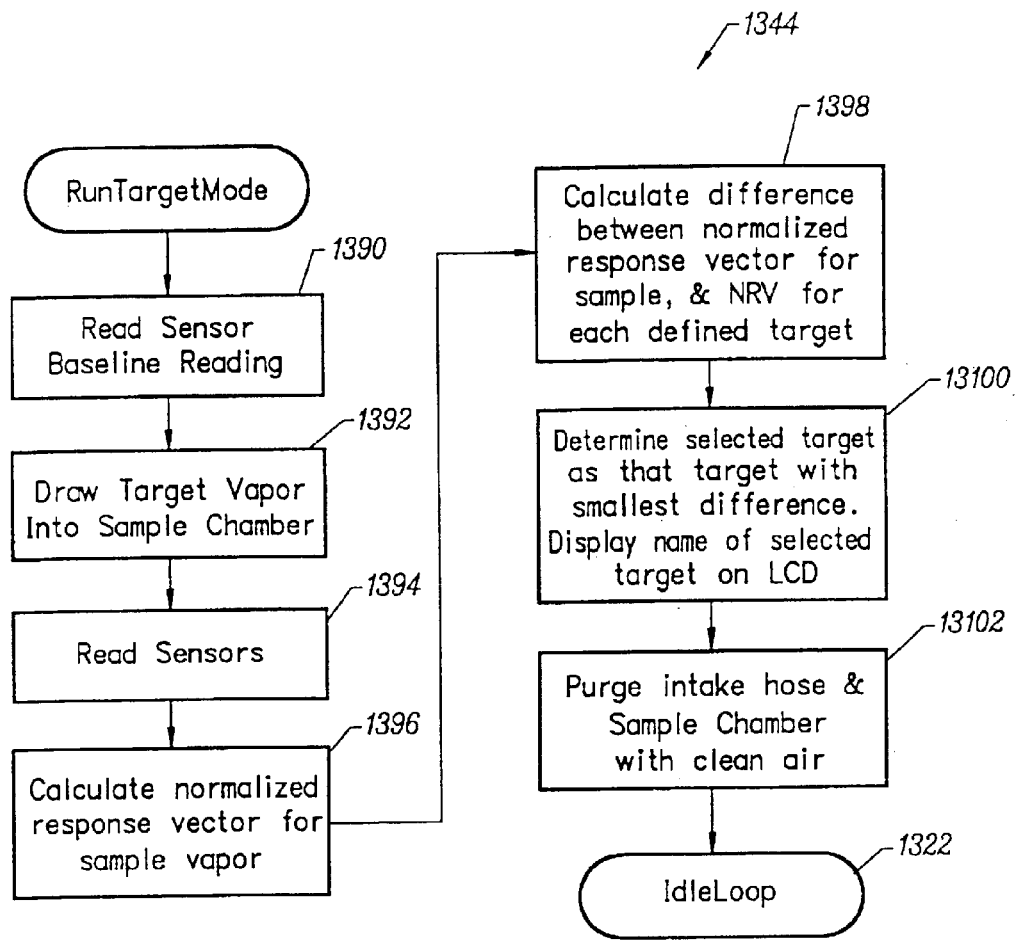

FIG. 13E shows a flow diagram of an embodiment of the identify mode subroutine. Steps 1390, 1392, 1394, and 1396 in FIG. 13E are similar to steps 1370, 1372, 1374, and 1376 in FIG. 13D, respectively. At a step 1398, the normalized response vector for the unknown sample calculated in step 1396 is compared with the normalize response vectors for the various target samples, as determined by earlier passes through the target mode subroutine (FIG. 13D) and stored in memory. Specifically, differences between the respective normalized response vectors are calculated at step 1398, and the smallest difference vector is determined (i.e., using a least mean square analysis), at a step 13100. Also at step 13100, the result of that determination is displayed on a display. Finally, at a step 13102, the pump and valve assembly are conditioned to draw clean air to the sample chamber(s). The identify mode subroutine then terminates, and the program returns to the idle loop (step 1322 in FIG. 13A).

Figures 13F, 13G:
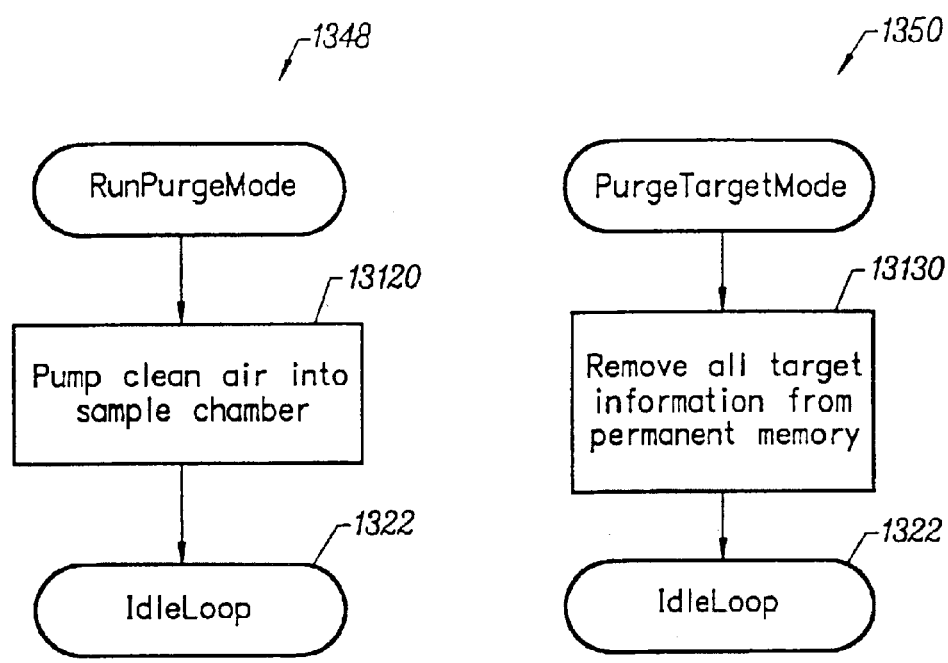

FIG. 13F shows a flow diagram of an embodiment of the purge mode subroutine. At a step 13120, the pump and valve assembly are conditioned to draw clean air into the sample chamber(s) via the intake port. The program then returns to the idle loop (step 1322 of FIG. 13A).

FIG. 13G shows a flow diagram of an embodiment of the purge target mode subroutine. At a step 13130, all of the target sample information stored in memory is erased. The program then returns to the idle loop (step 1322 in FIG. 13A).

Figure 14A:
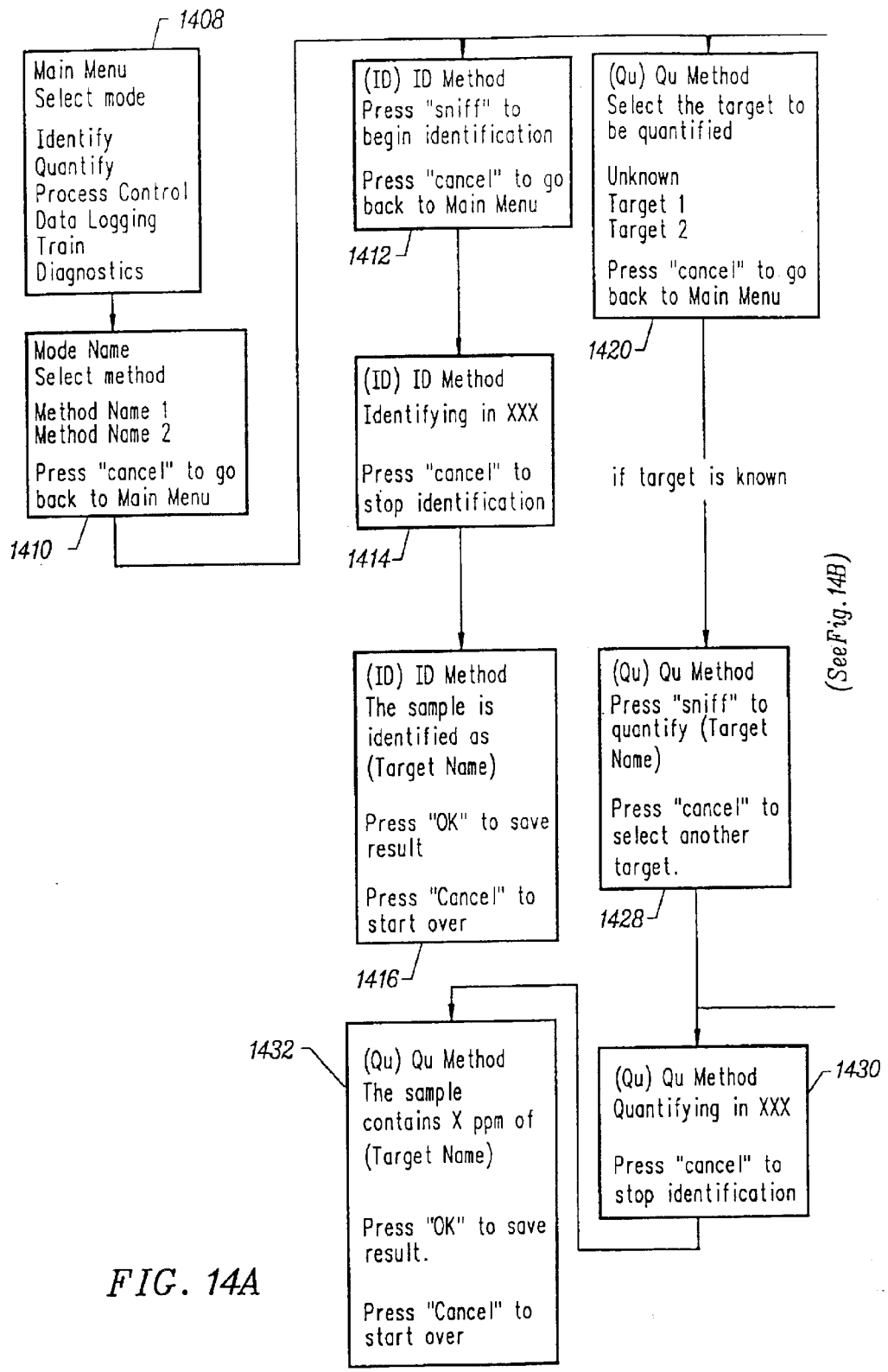
FIGS. 14A through 14C show a diagram of an embodiment of the menu selection for the e-nose device.
Figure 14B:
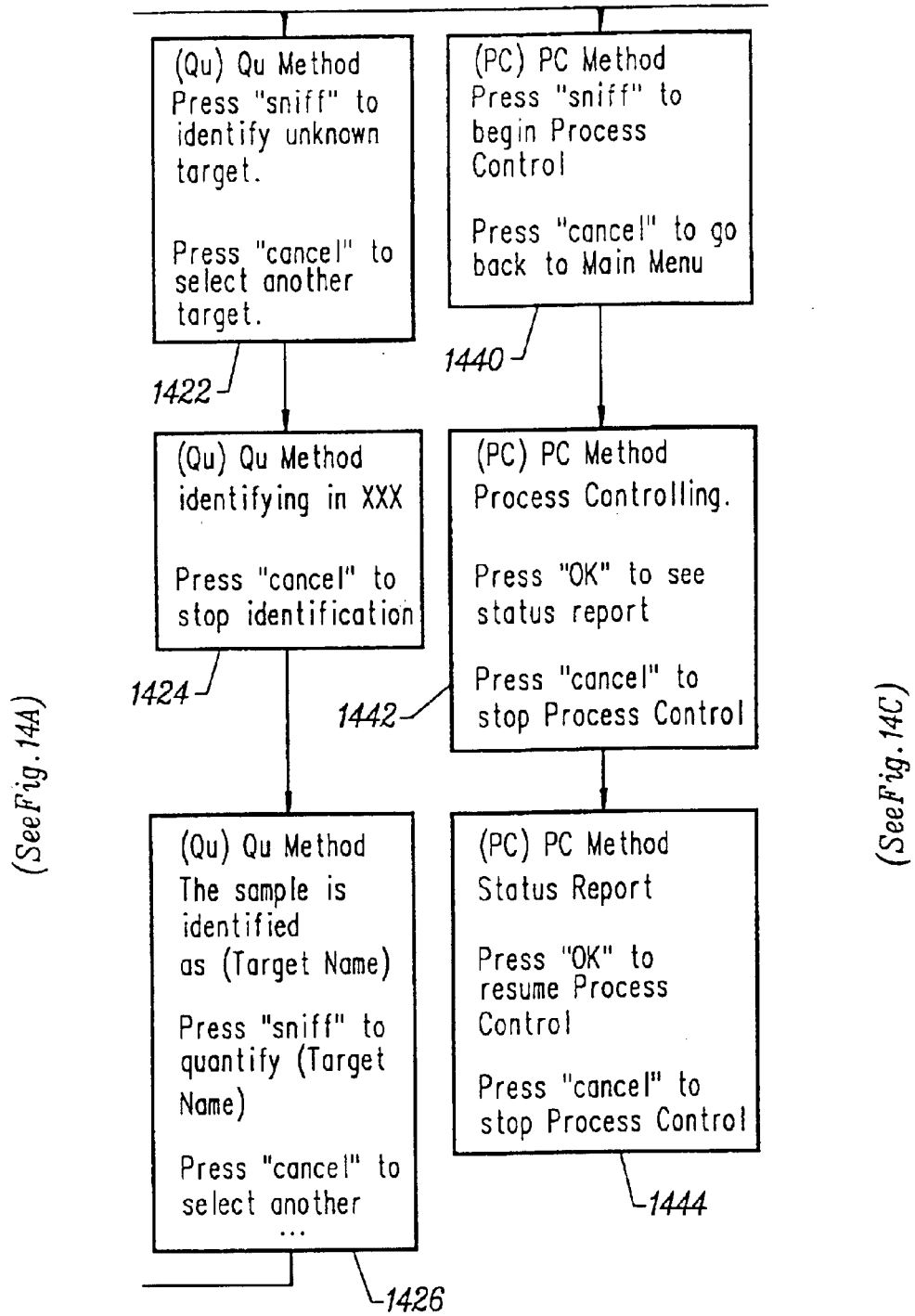
Figure 14C:
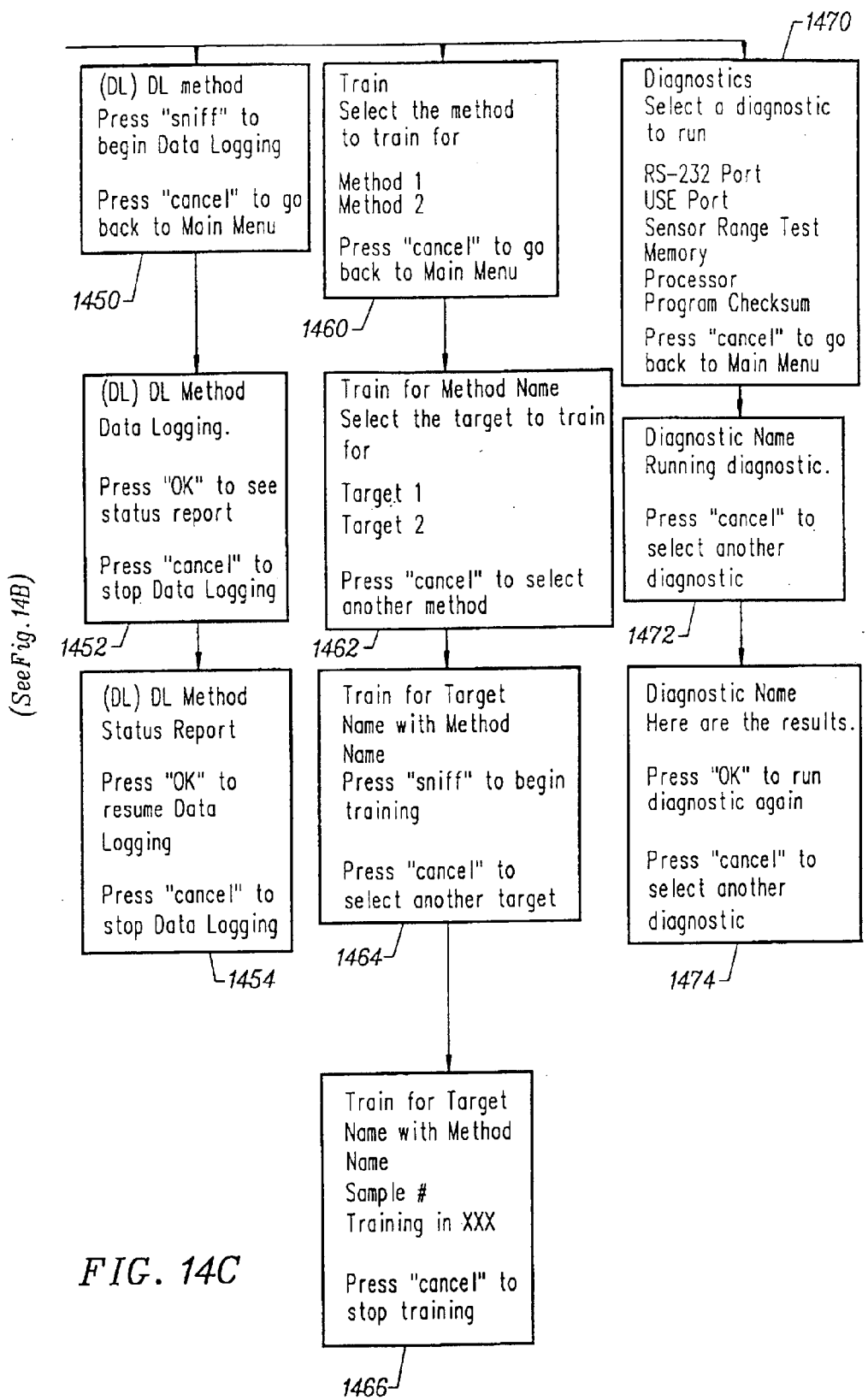

FIG. 14 shows a diagram of an embodiment of the menu selection for the e-nose device. In FIG. 14, a main menu 1408 displays the measurement modes available for the particular e-nose device. The available modes can be dependent, for example, on the particular modules installed in the e-nose device. In an embodiment, the following modes are available in the main menu: Identify, Quantify (Qu), Process Control (PC), Data Logging (DL), Train, and Diagnoses. Upon making a mode selection in menu screen 1408, a menu screen 1410 appears that queries the user to select a particular method from among a set of available methods.

By selecting the ID Method option, a menu screen 1412 appears that queries the user to press "sniff" to begin identification or "cancel" to return to the main menu. Upon selecting the sniff option, the e-nose device begins the identification process, as shown in a menu screen 1414, and provides the results upon completion of the process, as shown in a menu screen 1416. The user is provided with an option to save the results.

By selecting the Qu Method option, a menu screen 1420 appears that queries the user to select a target. If the identity of the target is unknown, a menu screen 1422 provides the user with the option of performing a sniff to identify the unknown target. Upon selecting the sniff option, the e-nose device begins the identification process, as shown in a menu screen 1424, and provides the identity upon completion of the process, as shown in a menu screen 1426. Once the sample is identified or if the identity is known initially, the target can be quantified in menu screens 1426 and 1428. The e-nose device begins the quantification process, as shown in a menu screen 1430, and provides the results upon completion of the process, as shown in a menu screen 1432.

By selecting the PC Method option, a menu screen 1440 appears that queries the user to press "sniff" to begin the process control or "cancel" to return to the main menu. Upon selecting the sniff option, the e-nose device begins the process control, as shown in a menu screen 1442, and provides the status report, as shown in a menu screen 1444.

By selecting the DL Method option, a menu screen 1450 appears that queries the user to press "sniff" to begin the data logging or "cancel" to return to the main menu. Upon selecting the sniff option, the e-nose device begins the data logging process, as shown in a menu screen 1452, and provides the status report, as shown in a menu screen 1454.

By selecting the Train option, a menu screen 1460 appears that queries the user to select one of a number of training methods. The user selects a particular method and a menu screen 1462 appears that queries the user to select one of a number of targets. The user selects a particular target and a menu screen 1464 appears that queries the user to press "sniff" to begin the training. Upon selecting the sniff option, the e-nose device begins the training process using the method and target selected by the user, as shown in a menu screen 1466.

By selecting the Diagnostics option, a menu screen 1470 appears that queries the user to select a diagnostic to run. Possible diagnostics include, for example, RS-232 port, USB port, sensor range test, memory, processor, and program check sum. The user selects a particular diagnostic and the e-nose device begins the selected diagnostic test, as shown in a menu screen 1472, and provides the diagnostic results, as shown in a menu screen 1474.

Modular Design

In certain aspects of the invention, the e-nose device is designed using modular sections. For example, the nose, filter, manifold, sensor module, power pack, processor, memory, and others can optionally be disposed within a module that can be installed or swapped, as necessary. The modular design provides many advantages, some of which are related to the following characteristics: exchangeable, removable, replaceable, upgradable, and non-static.

With a modular design, the e-nose device can be designed for use in wide variety of applications in various industries. For example, multiple sensor modules, filters, and so on, can be added as the list of samples to be measured expands.

In certain embodiments, the modular design can also provide improved performance. The various modules (i.e., nose, filter, manifold, sensor module, and so on) can be designed to provide accurate measurement of a particular set of test samples. Different modules can be used to measure different samples. Thus, performance is not sacrificed by the use of a small portable e-nose device. For example, to sense high molecular weight analytes, a certain particular nose chip is plugged in. Then, to analyze lower molecular weight analytes, another nose chip may be plugged in.

The modular design can also result in a cost effective e-nose design. Since some of the components can be easily replace, it is no longer necessary to dispose the entire e-nose device if a particular component wears out. Only the failed components are replaced.

In certain embodiments, the modular design can also provide an upgradable design. For example, the processor and memory module (individually or in combination) can be disposed within an electronic unit that can be upgraded with new technologies, or as required by on the particular application. Additional memory can be provided to store more data, by simply swapping out memory modules. Also, the analysis algorithms can be included in a program module that inserts into the e-nose device. The program modules can then be swapped as desired.

The modular design can also provide for disposable modules. This may be advantageous, for example, when analyzing toxic samples.

Nose

In the embodiments described above, the e-nose device includes an external sampling wand (or nose or snout). The nose can be attached to the device using a mechanical interconnect, such as a simple ¼-turn type, a threaded screw, a snap-on mechanical arrangement, and other interconnect mechanisms. Many materials can be used to fabricate the nose component, such as injection moldable materials.

In certain embodiments, the nose is interchangeable and uses a standard luer interconnection. The nose can be, for example, about 1 inch to about 50 inches in length and, preferably, the nose is about 6 inches to about 20 inches in length. The nose can optionally be ridged, or be a long flexi-hose or a flexible snorkel. In some embodiments, the nose has a luer needle on the smelling end. Optionally, the nose can withstand an internalized pressure and is joined with a pressured valve.

As shown in FIG. 3B, the nose can be dimensioned in various sizes and shapes. For example, nose 130d includes a wide opening that may be advantageous, for example, when sampling a gas. In contrast, nose 130f includes a pointed tip that is more suited for sampling at a specific site.

In some alternative embodiments, intake ports (such as intake port 132) can be used to receive test samples. The intake ports can substitute for, or supplement the external nose.

Sensor Modules

In certain aspects, the chemically sensitive sensors in the sensor module can be tailored to be particularly sensitive to particular classes of vapors. For example, the array for one such module can incorporate vapor sensors suitable for differentiating polar analytes such as water, alcohol, and ketones. Examples of polar polymers suitable for use as such vapor sensors include poly (4-vinyl phenol) and poly (4-vinyl pyrrolidone).

The sensor module can optionally be identified by means of an identification resistor (not shown) having a selected resistance. Thus, prior to processing the variable resistance measurements collected for the chemically sensitive resistors of each such sensor module, the processor measures the resistance of the identification resistor. In this manner, the nature of the module's chemically sensitive resistors can be initially ascertained.

A mechanism for detection of analytes is disclosed in the aforementioned PCT patent application Ser. No. WO99/08105.

Display

In some embodiments, the display is a liquid-crystal display (LCD). In other embodiments, the display is a graphical LCD that allows the device to display text and graphics. This type of display provides a quality product interaction experience. Examples of LCD modules include those manufactured by Epson Corporation, such as the EPSON EG7502 (TCM AO822) having a screen size of 57.56 mm by 35.99 mm, a 320×200 resolution with 0.8 dot pitch, and transflective and LED edge back light. Various other LCD modules are also suitable. Preferred LCD modules offer one or more of the following features: (1) higher resolution to allow for a smaller but comfortable display viewing areas (320×200 and fine dot pitch), (2) low power consumption (e.g., 3 mW to 9 mW), (3) multi-line scanning (active addressing) technology, (4) integrated "touch" panel, (5) integrated power supply and controller chips, (6) LED baklighting-for smaller module, (6) displays used with video, and other features.

Input Devices

In certain embodiments, the e-nose device optionally includes input devices, such as push buttons, a keypad, a keyboard, a touchscreen, switches, other input mechanisms, or a combination of the above. The keypad can be fabricated from various materials. In certain embodiments, the keypad is molded from silicone rubber, which advantageously provides tactile feedback for gloved hands. Moreover, navigational controls can optionally be incorporated into the keypad and buttons. For example, a "sniff" button can be optionally positioned into the keypad.

The keypad can optionally be a membrane type keypad. In this implementation, the keypad is formed from laminated sheets of acrylic, Mylar, PC, or other suitable materials. Snap domes can be used to achieve greater tactile feedback for the user. Product graphics can be incorporated into the keypad. Advantageously, the keypad has flexibility with graphics, is easy to clean, and has protection from spillage. In addition, the keypad is configured with low stroke distances. In certain other instances, a micro-switch, such as for a "sniff" button, is used to further accentuate the tactile "click" feedback and generate a low-level audible signal.

In certain embodiments, the e-nose device optionally includes a pointer. Advantageously, the pointer provides greater application flexibility and ease of use in the field. In certain aspects, the pointer can be used for bar code reading and easy inventory control. Further, the device optionally includes a pad. The pad allows for application flexibility, such as in field, training, or lab use.

The e-nose device optionally includes other input devices, such as a touch screen. Suitable touch screens include the analog resistive type. Other touch screens include those similar to the ones in PDA, GPS, and other products. Yet other touch screens include electromagnetic resonance types optionally having a dedicated stylus, such as a battery-less stylus. In addition, touch screens can include, but are not limited to, electrostatic, GSAW, and analog resistive and capacitive types. The analog resistive touch screen is preferred since high and low resolutions can readily be achieved.

In certain embodiments, the e-nose device notifies the user by providing general and specific information about the device's current mode. Operators of the device can see what options are available. Guidelines and instructions are available to assist the users interact with the product. In certain instances, the descriptions and instructions are brief and specific. Graphics and icons assist users through the product interaction. Users are provided with a mechanism to stop the device when necessary, and to return to previous screens where appropriate. These various features collaborate to provide device interactions that are quick, simple, and reliable.

In other embodiments, the e-nose device provides the users with information regarding the status of the device. Examples include, but are not limited to, initiating an action, performing an operation, waiting for input, and so on. Moreover, other device input and output parameters, such as hardware controls, include, but are not limited to: Scroll Up—keypad; (2) Scroll Down—keypad; (3) Select—keypad; (4) Cancel —keypad; (5) Sniff—keypad; (6) Power-on/Backlight on/off; (7) Digital Input—connector; (8) Analog Output—connector; (9) Serial out (RS232)—RJ11; (10) USB—Standard A; (11) Display contrast—(thumbwheel, analog pot); (12) System reset—pin hole; (13) Battery recharge—jack; (14) pneumatics ports; (15) nose inhale port (sample sniff port); (16) exhale (exhaust); and (17) reference intake.

Radiocard

In certain aspects, the device has wireless Ethernet capabilities such as a radiocard having a media access controller. The media access controller regulates the data from handheld device to other devices.

Power Pack

The e-nose device optionally includes a power pack, such as a battery, for providing electrical power. In certain embodiments, the device operates from power supply voltages of approximately 3.3 volts and approximately 5.0 volts DC. In a specific embodiment, the device consumes approximately 3.2 watts or less, with a typical average power consumption of approximately 1.8 watts. In an embodiment, the device is capable of operation from about 1 hour to about 20 hours without requiring a recharge of the power pack.

The power pack can be fabricated using nickel cadmium (NiCd), nickel-metal hydride (NiMH), lithium ion (Li-ion), sealed lead-acid (SLA), or other battery technologies. Preferably, the battery pack has low weight and a high power density to keep the volume of the battery small. Lithium-ion cells have a relatively high internal resistance and wider range of voltages during a discharge compared to other battery chemistries. A voltage regulator can be used to provide proper voltages for the circuitry within the e-nose device. For efficiency, a switching voltage regulator can be used in place of linear type regulators. The voltage regulator can also be used to provide multiple output voltages for different circuitry within the e-nose device. In certain instances, output voltages required from the power supply include values above and below the battery voltage. In these instances, a SEPIC topology for the switching regulator can optionally be used. Conversion efficiency of such switching regulators is approximately 85%. To provide approximately 18 watt-hours of energy to the load using such switching regulator, the energy requirement from the lithium-ion battery pack is approximately 21 watt-hours.

In a specific embodiment, a lithium-ion (Li-ion) battery pack of approximately 100 cubic centimeters (cc) in volume and about 250 grams in weight can optionally be used for the e-nose device. In another specific embodiment, a nickel-metal hydride (NiMH) battery pack can be used that weighs about 370 grams and has a volume of about 150 cc. Other batteries capable of providing an equivalent amount of energy include, but are not limited to, a nickel-cadmium (NiCd) battery pack of approximately 560 grams and 210 cc and a sealed lead-acid (SLA) battery pack of approximately 750 grams and 350 cc.

In general, charging times increase and the available battery capacity reduces for low (e.g., 0 to 10° C.) and high (e.g., 40 to 50° C.) temperatures. For accurate "gas gauging" under such conditions, the Smart Battery System (SBS) can also be employed. The SBS is part of a commercially available System Management Bus (SMB) system. The SBS allows battery packs to communicate to smart chargers and other system intelligence using a physical protocol similar to the I$^2$C bus protocol from Philips Corporation. The software protocol on the SMB allows for direct communication of parameters such as the state of charge, battery pack voltage, battery temperature, number of discharge cycles, and so on. Several vendors of integrated circuits now offer single chip implementations of the SMB interface. Alternatively, a custom programmed microcontroller, such as a PIC chip Microchip Technology Inc., can be used for this purpose.

In some embodiments, the device includes a power pack that is optionally chargeable. In some other embodiments, the device optionally includes batteries such as, for example, four AA cells. The cell chemistries can vary. The device optionally accommodates alkaline interchangeability.

The device optionally has a fitting for a secondary rechargeable pack that can be the same, or smaller, size as the power devices described above.

Specific Electronic-Nose Device Implementations

The e-nose device can be implemented in various configurations, to include various features, and be used in various applications. Some specific implementations are provided below.

In one specific implementation, the e-nose device includes a sensor array of 32 sensors, composed of conducting particles uniformly dispersed in a polymer matrix. Each polymer expands like a sponge when exposed to a test medium (e.g., vapor, liquid, gas), thereby increasing the resistance of the composite. The polymers expands to varying degrees because of their unique response to different analytes. This change in resistance varies across the sensor array, producing a distinctive signature response. Regardless of whether the analytes correspond to a complex mixture of chemicals in the test sample or from a single chemical, the e-nose device includes sufficient polymer arrays to produce a distinct electrical "fingerprint" for the samples of interest. The pattern of resistance changes in the sensor array is indicative of the identity of the analytes, while the amplitude of the pattern indicates the concentration of the analytes.

The normalized change in resistance is then transmitted to a processor that identifies the type, quantity, and quality of the vapor based on the detected pattern in the sensor array.

In another specific implementation, a portable e-nose device for use in the field to detect volatile compounds is fabricated according to the invention. The device incorporates an easy-to-read graphic LCD with back lighting and one or more light emitting diodes (LEDs) to indicate mode of operation. Communications ports are provided to enable easy downloading of data into a spreadsheet package. Rapid response time, combined with easy one-button operation, provide an effective and accurate measurement of the samples. Power is supplied by replaceable or rechargeable batteries. Housed in a robust, water-resistant case, the portable e-nose device is suitable for various environments.

In yet another specific implementation, the e-nose device is designed to acquire and store data collected from 32 independent sensor elements. The e-nose device includes a 32-channel sample chamber with inlet/outlet ports, a pump, a 3-way solenoid switch, a LCD, push buttons, LED, a humidity probe, a temperature probe, and a digital interface. In certain aspects, the temperature probe and the humidity probe can be used to measure the environment of the analyte.

The power supply is designed for a 9-volt DC input. A rectifying diode is added for circuit protection. Two on-board 5-volt linear regulators are utilized for the analog and digital circuitry, respectively. A high precision buried Zener diode is provided to supply a +2.5 volt reference. The overall design is a mixed 3V and 5V design for reduced power consumption in a handheld device.

The sample chamber houses 32 sensor elements deposited on four ceramic substrates, each with eight sensor elements. The substrates are fabricated using hybrid microelectronic co-fired ceramic (alumina) processes. Electrodes and contacts are deposited as thick films using screen-printing techniques. Resistive paths can be provided (e.g., three paths) to be used as heating elements. On the backside of the substrate, a surface mount thermistor can be placed to form a heating/cooling control loop.

An inlet port is provided and a baffle can be inserted to fan out the incoming sample stream. The outlet port is respective to ambient barometric pressures. The sample chamber can be fabricated of Teflon and is airtight, and is mount to the PCB. An on-board pump can push the sample flow into the sample chamber at pressures slightly higher than 14.7 psi. The on-board 3-way solenoid switch can switch under processor control between a known reference source (i.e., to "re-zero" or recalibrate as necessary) and an unknown test sample. The four ceramic substrates are inserted in two 20-pin, 50-mil spacing, dual row connectors. The spacing between the rows is 100 mils. A temperature probe is inserted into one connector and a humidity probe is inserted into the other. The temperature and humidity probes are used for diagnostics.

A biasing network can been implemented that biases the chemically sensitive resistor in a DC mode of operation. The network is a ratiometric network that is easy to implement and stable, and offers a wide dynamic range.

It has been shown that 50 PPM changes in electrical resistance of the chemically sensitive can be measured. Further, baseline changes greater than ±50% can be accounted for with minimal change in applied power, as shown in Table 1.

TABLE 1

Detectable Changes in Resistance for Various Baseline Resistances

| Baseline | Vout | Applied Power | Resolution |
|---|---|---|---|
| 15K (−Δ50%) | 0.326 | 0.047 | 18 bits |
| 20K (−Δ33%) | 0.417 | 0.043 | 18 bits |
| 25K (−Δ17%) | 0.500 | 0.040 | 17 bits |
| 30K, nominal resistance | 0.577 | 0.037 | 17 bits |
| 35K (+Δ17%) | 0.648 | 0.034 | 17 bits |
| 40K (+Δ33%) | 0.714 | 0.032 | 17 bits |
| 45K (+Δ50%) | 0.776 | 0.030 | 17 bits |

Assuming that Johnson noise is the dominant noise source, it is possible to calculate an average noise voltage of 0.3 $\mu V$ over a 10 Hz bandwidth and can thus detect these step changes. By keeping the current low (i.e., <25 $\mu A$) the $1/f$ noise is reduced. In general, the biasing scheme is a constant voltage, DC system. The current is limited to micro-amperes ($\mu As$) per sensor element and the applied power is in the order of micro-watts ($\mu Ws$). For added flexibility the current is limited and the output voltage is scaled by resistors.

The handheld sensing apparatus of the present invention was used to sense a series of four (4) homologous ester analytes. The analytes sensed were the ethyl esters of propionate, butyrate, valerate, and hexanoate. The response data was then analyzed using principal component analysis. Principal Component Analysis (PCA) is a powerful visualization tool that provides a way to reduce the dimensionality of the data. PCA finds linear combinations of the original independent variables that account for maximal amounts of variation and provides the best possible view of variability in the independent variable block. Natural clustering in the data is readily determined.

Figure 15:
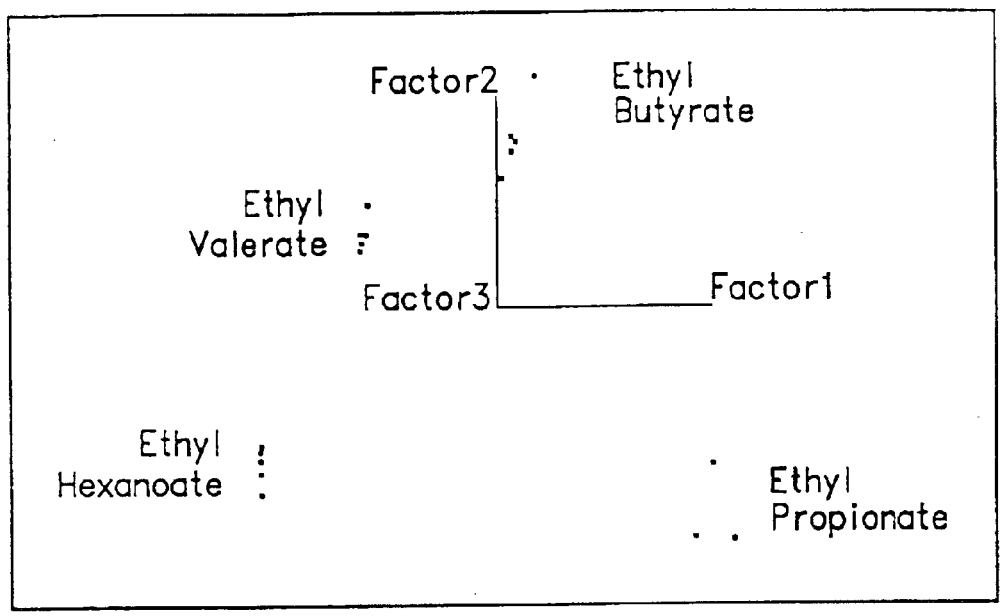
FIG. 15 shows a graph of a principal component analysis of the responses to a series of esters using the handheld apparatus of the present invention.

FIG. 15 shows a graph of a principal component analysis of the responses to a series of esters using the handheld apparatus. As shown in FIG. 15, the ester analytes were well discriminated by the handheld device.

Analytes and Applications of the E-Nose Device

Analytes detectable by the e-nose device of the invention include, but are not limited to, alkanes, alkenes, alkynes, dienes, alicyclic hydrocarbons, arenes, alcohols, ethers, ketones, aldehydes, carbonyls, carbanions, heterocycles, polynuclear aromatics, organic derivatives, biomolecules, microorganisms, bacteria, viruses, sugars, nucleic acids, isoprenes, isoprenoids, and fatty acids and their derivatives. Many biomolecules, such as amino acids, are amenable to detection using the sensor arrays of the invention.

The e-nose device can be used to enable medical and dental care-providers to quickly and accurately identify the chemical components in breath, wounds, and bodily fluids to diagnose a host of illness including infections and metabolic problems. For example, the e-nose device can be used to test for skin conditions, for anesthesia administration, or to determine time of ovulation in fertility treatment. Moreover, the device can be used in genomic assays and target-based pharmaceutical screening. Alternatively, the handheld device can classify and identify microorganisms, such as bacteria.

The e-nose device can be used to locate an odor to identify a complicated system or state of matter, and can offer versatility and reliability absent from conventional environmental or chemical monitoring devices. Advantageously, the device can be used for profiling a chemical environment in a hazardous materials situation and to assist emergency crews to accurately select fire retardant, containment strategies, and protective gear. The e-nose device can be used to detect leaks in pipelines and storage containers.

The e-nose device can be used in food quality and processing control. For example, the device can be used to spot test for immediate results or to continually monitor batch-to-batch consistency and spoilage in various stages of a product, including production (i.e., growing), preparation, and distribution. The device can also be used in disposable packaging to providing an objectivity that is absent from conventional spoilage, freshness, and contamination monitoring techniques.

The e-nose device can also be used in protecting the elderly, who tend to lose sense of smell over time. The device can be used to reduce the risk of food poisoning or the ingestion of spoiled food, and can be integrated with household appliances, such as refrigerators and microwave ovens.

The e-nose device can be used in a wide variety of commercial applications including, but not limited to:

applications such as utility and power, oil/gas petrochemical, chemical/plastics, automatic ventilation control (cooking, smoking, etc.), heavy industrial manufacturing, environmental toxicology and remediation, biomedicine, cosmetic/perfume, pharmaceutical, transportation, emergency response and law enforcement, detection, identification, and/or monitoring of combustible gas, natural gas, $H_2S$, ambient air, emissions control, air intake, smoke, hazardous leak, hazardous spill, fugitive emission, hazardous spill, beverage, food, and agricultural products monitoring and control, such as freshness detection, fruit ripening control, fermentation process, and flavor composition and identification, detection and identification of illegal substance, explosives, transformer fault, refrigerant and fumigant, formaldehyde, diesel/gasoline/aviation fuel, hospital/medical anesthesia & sterilization gas, telesurgery, body fluids analysis, drug discovery, infectious disease detection and breath applications, worker protection, arson investigation, personal identification, perimeter monitoring, fragrance formulation, and solvent recovery effectiveness, refueling operations, shipping container inspection, enclosed space surveying, product quality testing, materials quality control, product identification and quality testing.

Figure 16:
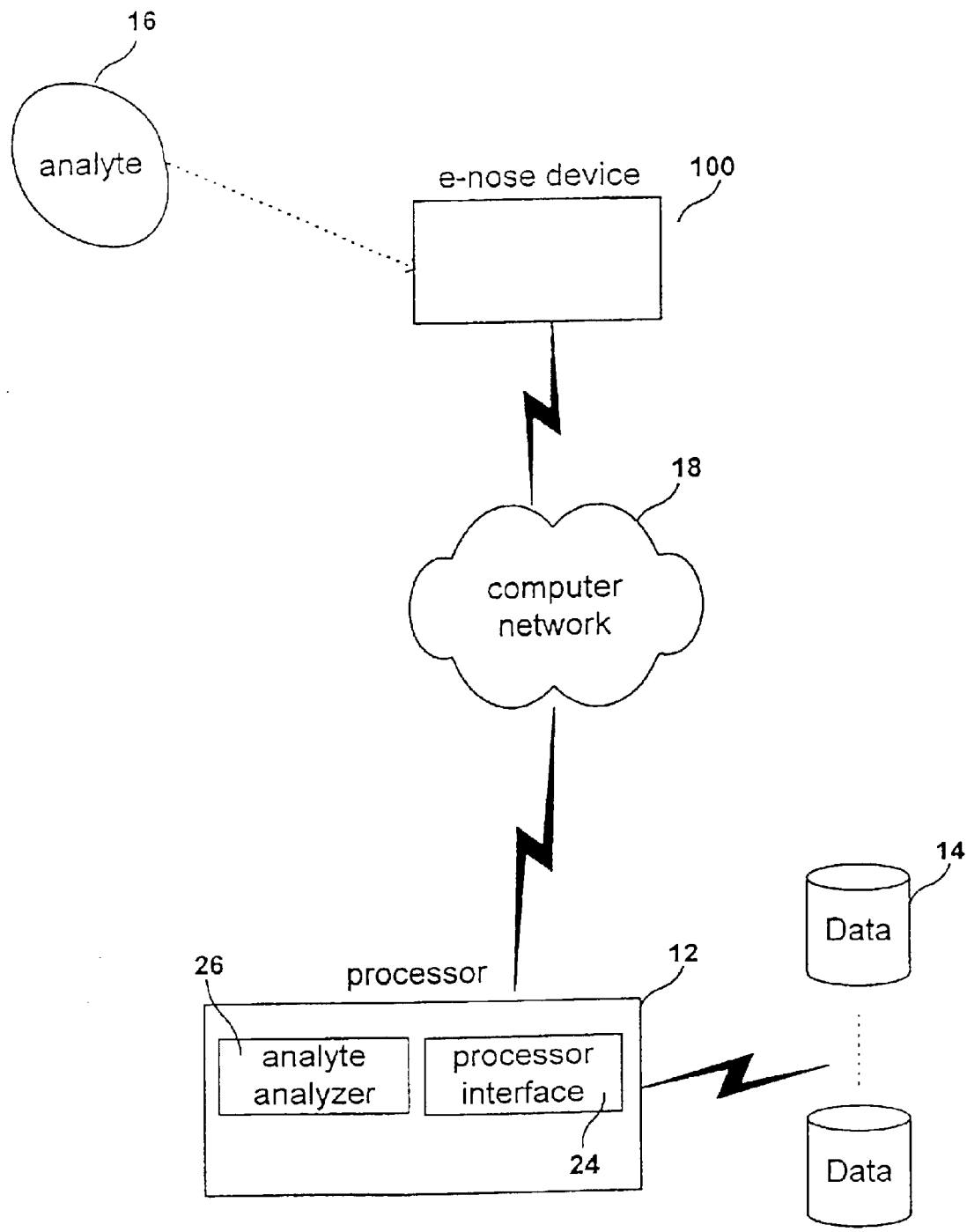
FIG. 16 is a simplified schematic block diagram showing one mode of operation of the present invention.

The e-nose device 100 can be used to detect and capture analyte data and subsequently transmit such data to the outside world over a computer network for analysis at a remote location. FIG. 16 is a simplified schematic block diagram showing one mode of operation of the present invention. In this mode of operation, the e-nose device 100 detects an analyte 16 and subsequently transmits the data relating to such analyte via a computer network 18 to the processor 12 for analysis. The data communications between the e-nose device 100 and the processor 12 can be either one-way or two-way communication. The e-nose device 100 can act solely as a transmitter capable of only sending data to the processor 12, or alternatively, the e-nose device 100 can act as a transceiver capable of both sending and receiving data from the processor 12. In addition, e-nose devices 100 may also be able to communicate with one and other.

The processor 12 includes a processor interface 24 and an analyte analyzer 26. The main function of the processor interface 24 is to handle data communications between the processor 12, the e-nose device 100 and the electronic library 14. The processor interface 24 receives data from the e-nose device 100 via the computer network 18 and processes the data into a format that can be understood by the analyte analyzer 26. When necessary, the processor interface 12 also interacts with the electronic database 14 to retrieve data therefrom for analytical purposes or update the electronic database 14 with new data.

The analyte analyzer 26 is capable of performing analysis on a detected analyte. Using data stored in the electronic library 14, the analyte analyzer 26 compares data received from the e-nose device 100 with data retrieved from the electronic database 14 via the processor interface 24 to identify the identity of the detected analyte.

The method and system of the present invention include the use of pattern recognition algorithms to compare the output signature of the detected unknown analyte to the signatures of known analytes. Many of the algorithms are neural network based algorithms. A neural network has an input layer, processing layers and an output layer. The information in a neural network is distributed throughout the processing layers. The processing layers are made up of nodes that simulate the neurons by its interconnection to their nodes.

In operation, when a neural network is combined with a sensor array, the sensor data is propagated through the networks. In this way, a series of vector matrix multiplications are performed and unknown analytes can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In a preferred embodiment, the Fisher linear discriminant analysis (FLDA) and canonical discriminant analysis (CDA) and combinations thereof are used to compare the output signature and the available data from the electronic library. The operating principles of various algorithms suitable for use in the present invention are disclosed (see, Shaffer et al., *Analytica Chimica Acta*, 384, 305–317 (1999)), the teaching of which are incorporated herein by reference.

With respect to the electronic library 14, it generally contains signatures for various known analytes and other relevant information pertaining to these analytes. The electronic library 14 can be composed of a number of different databases. These databases can be located in one central depository, or alternatively, they can be dispersed among various distinct physical locations. These databases can be categorized and structured in various ways based on the needs and criteria of the database designer. For example, a first database may contain data relating to various types of analytes collected using the same detection technique under a standardized set of conditions, and a second related database may contain miscellaneous information correlating to data contained in the first database. Alternatively, a database may contain data specific to one particular analyte with such data collected using different detection techniques. Methods used to create and organize databases are commonly known in the art, for example, relational database techniques can be used to logically connect these databases.

The databases comprising the electronic library 14, or a portion thereof, can be physically located separate from the processor 12. These databases can reside on remote, distant servers on a local area network or the Internet. Under this arrangement, whenever any data are needed, the processor 12 needs to access the necessary database(s) via a communication channel to retrieve the requisite data for analysis. For example, the processor 12 can access and retrieve data from a remote database via a computer network such as a LAN or the Internet.

A number of different technologies can be used to implement the communications between the e-nose device 100, the processor 12 and the electronic library 14. As to communications between the e-nose device 100 and the processor 12, such communications can be conducted via a computer network 18. The computer network 18 can be one of a variety of networks including a worldwide computer network, an internet, the Internet, a WAN, a wireless network, a LAN or an intranet. It should be understood that conventional access to the computer network is conducted through a gateway (not shown). A gateway is a machine, for example, a computer that has a communication address recognizable by the computer network 18.

Figure 17:
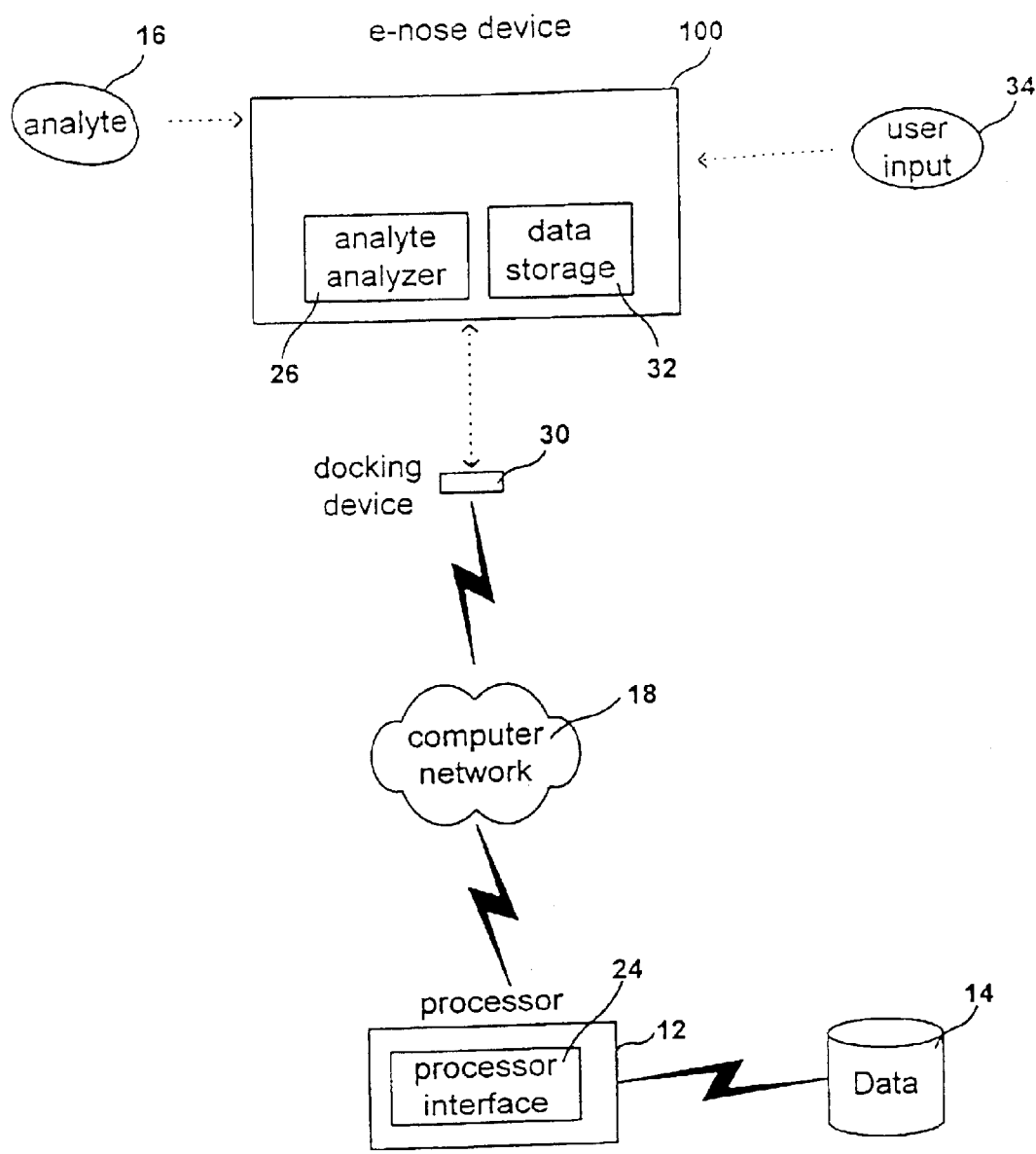
FIG. 17 is a simplified schematic block diagram showing another mode of operation of the present invention.

The e-nose device 100 can communicate to the outside world via a computer network 18 using either wireless or wired technologies. Wireless technologies may include infrared, radio waves, and microwaves. Wired technologies may include cables and modems. For example, as shown in FIG. 17, the e-nose device 100 can be detachably coupled to a docking device 30 which, in turn, is connected to a gateway on the computer network 18.

Figure 18:
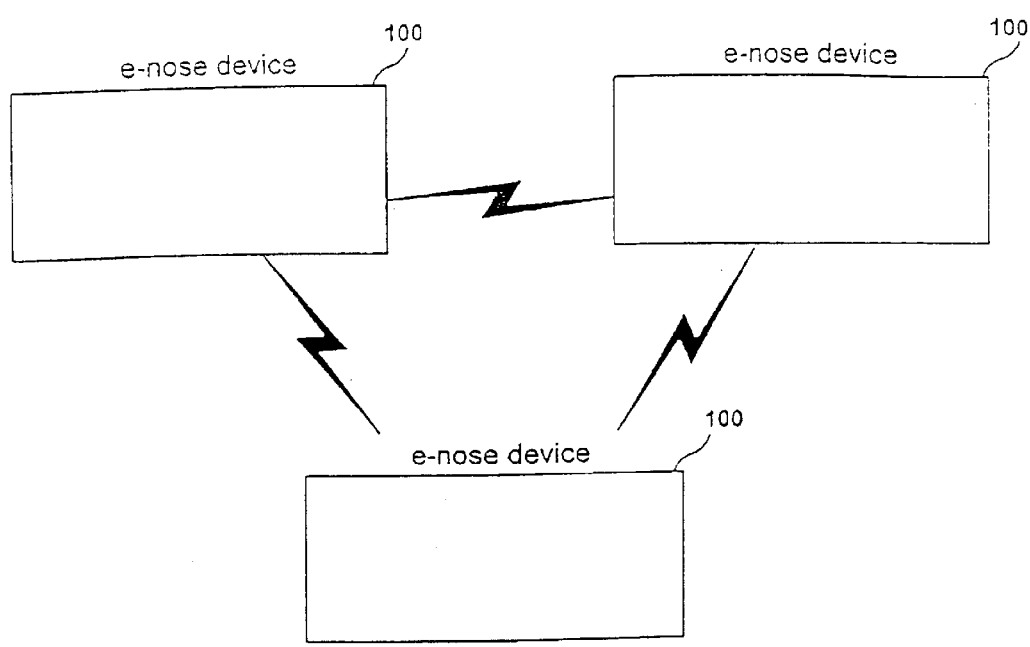
FIG. 18 is a simplified schematic block diagram showing yet another mode of operation of the present invention.

Furthermore, as mentioned above and shown in FIG. 18, e-nose devices 100 may be able to communicate with one another directly. In this device-to-device type of communication, infrared signals are generally used.

As to communications between the processor 12 and the electronic library 14, the communications can also be conducted via a computer network. As mentioned above, depending on various requirements, the electronic library 14 can reside on the same machine as the processor 12, thereby reducing communication overhead and costs.

The e-nose device 100 generally performs the following steps before the captured analyte data are delivered to the computer network 18 for transmission: (1) capturing analyte data in analog form; (2) converting the analog data into electrical data; (3) encoding electrical data into an analysis format; (4) encoding data in analysis format into a TCP/IP format; and (5) encoding data in TCP/IP format into a specific network data format. At the receiving end, the processor 12 generally performs the following steps to decode the encoded data: (1) receiving data in specific network data format; (2) decoding the received data into TCP/IP format; and (3) decoding the data in TCP/IP format into an analysis format.

Figure 19:
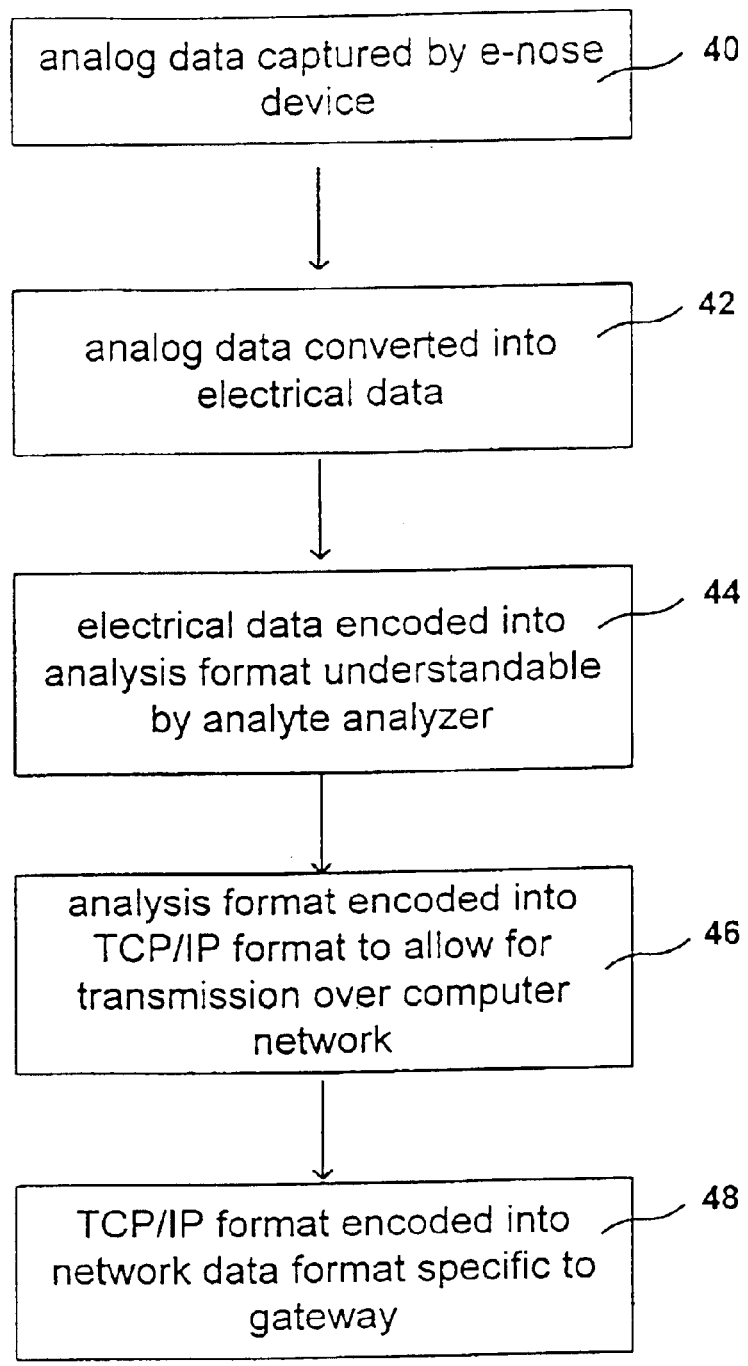
FIG. 19 is a simplified flow diagram showing the process of encoding the data by the e-nose device.

Details of these steps will now be described with reference to FIGS. 19 and 20. FIG. 19 illustrates the various data encoding formats needed to convert the analog data from the detected analyte into a transmissible format for transmission to the processor 12. At step 40, analog data from the detected analyte are first captured by the e-nose device 100. The analog data are converted into electrical signals at step 42. At step 44, the electrical signals are encoded into an analysis format that can be understood by the analyte analyzer 26. This format can be either proprietary or well-known. Any format can be used as long as the analyte analyzer 26 is capable of handling such format. While it is not necessary that the format used by the e-nose device 100, the processor 12, and the electronic library 14 be the same, a standardized format is preferred since format-conversion overhead can be saved. At step 46, the formatted data are further encoded into a format that can be transmitted over the computer network 18, such as the TCP/IP format. This step 46 is important if the formatted data are to be sent to the processor 12 via a computer network 18, such as the Internet, which contains numerous sub-networks having different network data formats. At step 48, the data in TCP/IP format are encoded into the specific network data format that the gateway to the computer network 18 can understand.

Figure 20:
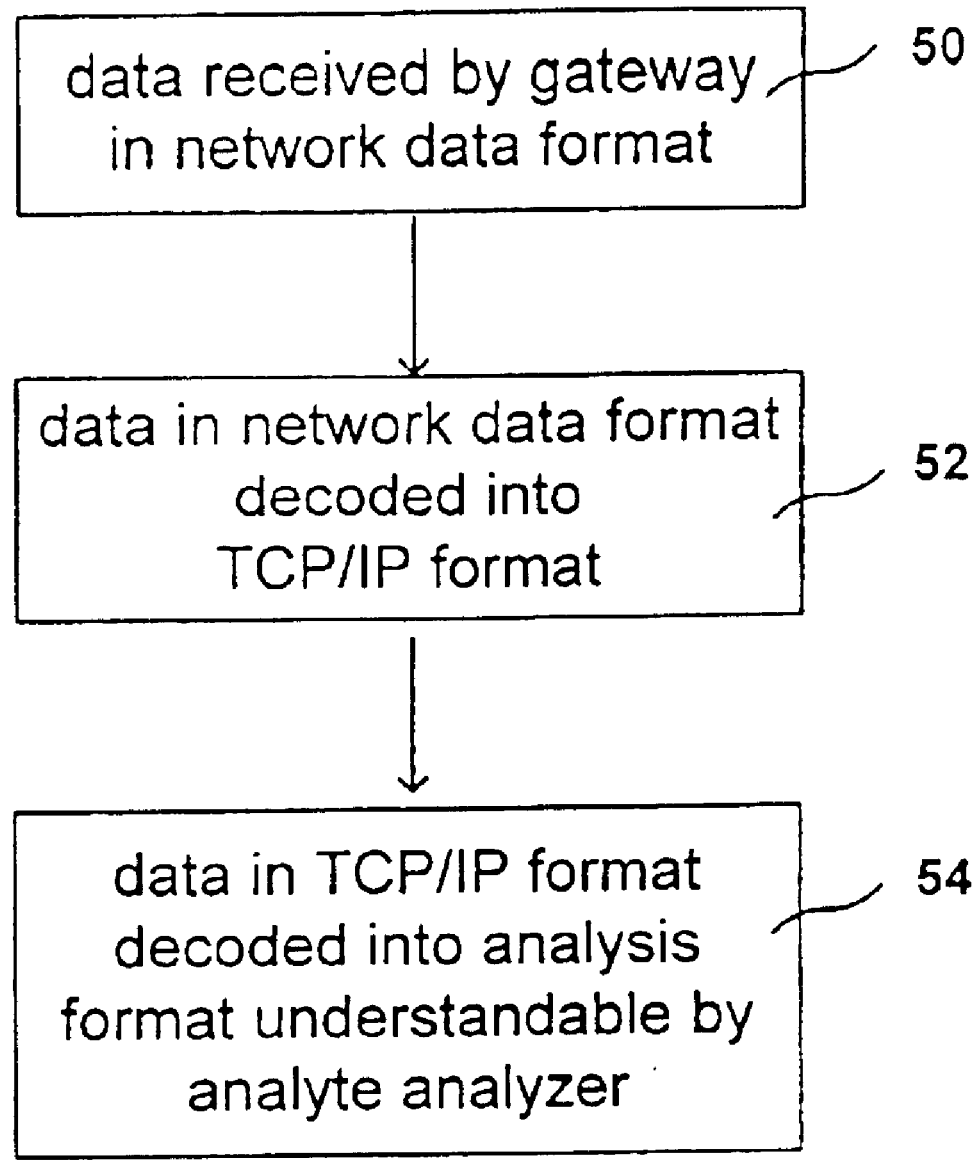
FIG. 20 is a simplified flow diagram showing the process of decoding the data sent by the e-nose device.

FIG. 20 illustrates the various data decoding formats needed to convert the transmitted data received from the e-nose device 100 to permit analysis by the processor 12. At step 50, data transmitted from the e-nose device 100 via the computer network 18 are received by the gateway in a network data format specific to the gateway. At step 52, the data in the network data format are decoded into the TCP/IP format. At step 54, the data in TCP/IP format are further decoded into an analysis format that can be used by the analyte analyzer 26 for analysis.

In another mode of operation, e-nose devices 100 are capable of communicating and exchanging data with one another. The primary purpose here is to allow sharing of data between two e-nose devices 100. In the event that multiple e-nose devices 100 (employing the same detection technique) are used to detect the same unknown analyte, data collected from these devices 100 can be used by the processor 12 for calibration purposes to provide for any use-to-use variability of a e-nose device 100.

In an alternate embodiment, as shown in FIG. 17, certain components of the processor 12, such as the analyte analyzer 26, can reside within the e-nose device 100. The analyte analyzer 26 is included within the e-nose device 100 as opposed to the processor 12 and the e-nose device 100 further includes a data storage area 32. With this particular configuration, the present invention may be operated in the following manner. The user enters a request 34 into the e-nose device 100 for data relating to certain specified, known analytes. The e-nose device 100 then transmits the request 34 to the processor 12. The processor 12, in turn, retrieves the relevant data from the electronic library 14 in accordance with the request 34 and forwards the requested data to the e-nose device 100. Upon receipt of the requested data, the e-nose device 100 stores them in a data storage area 32 for subsequent use. When the e-nose device 100 is used to detect an unknown analyte 16, data in the data storage area 32 are readily available for use by the analyte analyzer 26 to compare and identify the detected analyte 16.

By having the analyte analyzer 26 and the data storage area 34 incorporated into the e-nose device 100, the time required for analysis can be shortened. For example, prior to entering a particular area, if the user knows that there is a relatively high probability of presence of certain known analytes in that area, the user can download the signatures of these known analytes onto the e-nose device 100 ahead of time. With the signatures readily available within the e-nose device 100, the output signature of the detected analyte 16 can be compared against these known signatures first. Therefore, there may not be a need to connect to the processor 12 thereby allowing the analysis to be performed more quickly. Connection to the processor 12 only needs to be made when none of the downloaded signatures matches with that of the detected analyte 16.

It should be appreciated from the foregoing description that the present invention provides an apparatus for detecting and transmitting sensory data of analytes over a computer network. Although the invention has been described in detail with reference to the presently preferred embodiments, those of ordinary skill in the art will appreciate that various modifications can be made without departing from the invention. Accordingly, the invention is defined only by the following claims.

What is claimed is:

1. A method for transferring sensory data over a computer network for a diagnostic purpose, wherein said sensory data relates to identifying components in wounds and body cavities, said method comprising:

transmitting sensory data from a sensory device to a remote location;

receiving said sensory data at said remote location; and processing said sensory data at said remote location for diagnostic purpose.

2. The method of claim 1, wherein said sensory device is a handheld device.

3. The method of claim 1, wherein said computer network is a member selected from a group consisting of a wide area network, a local area network, an intranet, a worldwide computer network, and the Internet.

4. The method of claim 3, wherein said computer network is a wireless network.

5. The method of claim 4, wherein the wireless network is implemented using technologies selected from the group consisting of infrared, radio waves, satellite and microwaves technologies.

6. The method of claim 1, wherein said sensory data is a member selected from a group consisting of physical, chemical, taste, olfaction, optical olfaction, optical parameters or combinations thereof.

7. The method of claim 1, wherein said sensory data relates to genomic assays and target-based pharmaceutical screening.

8. A system for perimeter monitoring from a plurality of different remote locations to be distributed over a computer network, said system comprising:

a sensory device for measuring sensory data at the different locations that is coupled to said computer network, wherein said sensory device comprises at least one sensor which is a member selected from the group consisting of a conducting/nonconducting regions sensor, a quartz microbalance sensor, a conductive composite sensor, a chemiresistor and a fiber optical chemical sensor; and a wireless communication interface coupled to said sensory device and configured to communicate with said computer network situated at a remote location.

9. The system of claim 8, wherein said wireless communication interface is selected from the group consisting of an infrared data link, an optical interface, a microwave link and an RF interface.

10. The system of claim 9, wherein said wireless communication interface is an RF interface.

11. The system of claim 8, wherein said sensory device is a portable device.

12. The system of claim 8, wherein said sensory device comprises an analyte analyzer.

13. The system of claim 8, wherein said computer network comprises an analyte analyzer.

14. The system of claim 8, wherein sensory data selected from the group consisting of physical, chemical, taste, olfaction, optical parameters or combinations thereof.

15. The system of claim 8, wherein said sensory device is capable of detecting chemical, biological or explosive analytes.

16. The system of claim 8, wherein said system for perimeter monitoring is useful for the detection, identification, and monitoring of a combustible gas, natural gas, $H_2S$, ambient air, emissions control, air intake, smoke, a hazardous leak, a hazardous spill and a fugitive emission.

17. The system of claim 8, wherein said system for perimeter monitoring is useful for the detection and identification of illegal substances, explosives, a transformer fault, a refrigerant, a fumigant, formaldehyde, diesel fuel, gasoline fuel, aviation fuel, medical anesthesia and sterilization gas.

18. The system of claim 8, wherein said system for perimeter monitoring is useful for infectious disease detection.

19. The system of claim 8, wherein said system for perimeter monitoring is useful for shipping container inspection and enclosed space surveying.

20. The system. of claim 8, wherein said system for perimeter monitoring is suitable for the monitoring and control of beverage, food and agricultural products.

21. A system for detection and identification of explosives from a plurality of different remote locations to be distributed over a computer network, said system comprising:

a sensory device for measuring sensory data at the different locations that is coupled to said computer network wherein said sensory device comprises at least one sensor which is a member selected from the group consisting of a conducting/nonconducting regions sensor, a quartz microbalance sensor, a conductive composite sensor, a chemiresistor and a fiber optical chemical sensor; and a wireless communication interface coupled to said sensory device and configured to communicate with said computer network situated at a remote location.

22. A system for perimeter monitoring from a plurality of different remote locations to be distributed over a computer network, said system comprising:

a sensory device for measuring taste or flavor at the different locations that is coupled to said computer network; and a wireless communication interface coupled to said sensory device and configured to communicate with said computer network situated at a remote location.

* * * * *